United States Patent [19]

Lynch et al.

[11] Patent Number: 5,620,889
[45] Date of Patent: Apr. 15, 1997

[54] HUMAN ANTI-FAS IGG1 MONOCLONAL ANTIBODIES

[75] Inventors: David H. Lynch; Mark R. Alderson, both of Bainbridge Island, Wash.

[73] Assignee: Immunex Corporation, Seattle, Wash.

[21] Appl. No.: 322,805

[22] Filed: Oct. 13, 1994

Related U.S. Application Data

[63] Continuation-in-part of Ser. No. 159,003, Nov. 29, 1993, abandoned, which is a continuation-in-part of Ser. No. 136,817, Oct. 14, 1993, abandoned.

[51] Int. Cl.$^6$ ............... C12N 5/12; C07K 16/18; C07K 16/22; C07K 16/28
[52] U.S. Cl. ............ 435/332; 530/388.2; 530/388.24; 530/388.23; 530/387.1; 530/388.75; 435/334; 435/343.2; 424/144.1
[58] Field of Search ............ 435/240.27; 530/388.2, 530/388.24, 388.23, 387.1, 388.75

[56] References Cited

FOREIGN PATENT DOCUMENTS

0510691A1 10/1992 European Pat. Off. .
WO91/10448 7/1991 WIPO .

OTHER PUBLICATIONS

Dhein et al., *J. Immunology,* 149(10):3166–3174 (1992).
Itoh et al., *Cell,* 66:233–243 (1991).
Klas et al., *International Immunology,* 5:625–630 (1993).
Kobayashi et al., *Proc. Natl. Acad. Sci., USA,* 87:9620–9624 (1990).
Miyawaki et al., *J. Immunology,* 149(11):3753–3758 (1992).
Ogasawara et al., *Nature,* 364:806–809 (1993).
Trauth et al., *Science,* 245:301–305 (1989).
Yonehara et al., *J. Exp. Med.,* 169:1747–1756 (1989).
Owen–Schaub et al., *Cellular Immunology,* 140:197–205 (1992).
Jian et al., *Arthritis and Rheumatism,* 36(Suppl 9):s52, Abstract No. 80 (1993).
Zhou et al., *Arthritis and Rheumatism,* 36(Suppl 9):s52, Abstract No. 81 (1993).
Sevier et al., *Clin. Chem.,* 27(11):1797–1806 (1981).
Allen et al., *J. Exp. Med.,* 172:1367–1375 (1990).
Winter et al., *TIPS,* 14:139–143 (1993).
Alderson et al., *J. Exp. Med.,* 178:2231–2235 (1993).
Rhein, *Biotechnology Newswatch,* pp. 1 and 3 (1993).
Itoh et al., *J. Immunol.,* 151:621–627 (1993).

*Primary Examiner*—Susan A. Loring

[57] ABSTRACT

The present invention provides a panel of monoclonal antibodies and binding proteins which specifically bind to human Fas antigen. Some of the antibodies and binding proteins are capable of stimulating T cell proliferation, inhibiting binding of anti-Fas CH-11 monoclonal antibody to cells expressing Fas antigen, blocking anti-Fas CH-11 monoclonal antibody-mediated lysis of cells, and blocking Fas ligand-mediated lysis of cells. The invention also provides for therapeutic compositions comprising the monoclonal antibodies.

25 Claims, 10 Drawing Sheets

CD3

CD3 + hu Fas(M38)

CD3

CD3 + hu Fas(M38)

CD3

CD3 +
hu Fas(M38)

CD3

CD3 +
hu Fas(M38)

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
       ( A ) LENGTH: 31 base pairs
       ( B ) TYPE: nucleic acid
       ( C ) STRANDEDNESS: single
       ( D ) TOPOLOGY: unknown ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

| | | | |
|---|---|---|---|
| CTCGGTACCA | ACAACCATGC | TGGGCATCTG G | 31 |

( 2 ) INFORMATION FOR SEQ ID NO:2:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: unknown ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

| | | | |
|---|---|---|---|
| CAAGTTAGAT | CTGGATCCTT | CCTC | 24 |

( 2 ) INFORMATION FOR SEQ ID NO:3:

( i ) SEQUENCE CHARACTERISTICS:
       ( A ) LENGTH: 693 base pairs
       ( B ) TYPE: nucleic acid
       ( C ) STRANDEDNESS: single
       ( D ) TOPOLOGY: unknown ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

| | | | | | |
|---|---|---|---|---|---|
| AGATCTTGTG | ACAAAACTCA | CACATGCCCA | CCGTGCCCAG | CACCTGAACT | CCTGGGGGGA | 60
| CCGTCAGTCT | TCCTCTTCCC | CCCAAAACCC | AAGGACACCC | TCATGATCTC | CCGGACCCCT | 120
| GAGGTCACAT | GCGTGGTGGT | GGACGTGAGC | CACGAAGACC | CTGAGGTCAA | GTTCAACTGG | 180
| TACGTGGACG | GCGTGGAGGT | GCATAATGCC | AAGACAAAGC | CGCGGGAGGA | GCAGTACAAC | 240
| AGCACGTACC | GGGTGGTCAG | CGTCCTCACC | GTCCTGCACC | AGGACTGGCT | GAATGGCAAG | 300
| GAGTACAAGT | GCAAGGTCTC | CAACAAAGCC | CTCCCAGCCC | CCATCGAGAA | AACCATCTCC | 360
| AAAGCCAAAG | GGCAGCCCCG | AGAACCACAG | GTGTACACCC | TGCCCCCATC | CCGGGATGAG | 420
| CTGACCAAGA | ACCAGGTCAG | CCTGACCTGC | CTGGTCAAAG | GCTTCTATCC | CAGCGACATC | 480
| GCCGTGGAGT | GGGAGAGCAA | TGGGCAGCCG | GAGAACAACT | ACAAGACCAC | GCCTCCCGTG | 540
| CTGGACTCCG | ACGGCTCCTT | CTTCCTCTAC | AGCAAGCTCA | CCGTGGACAA | GAGCAGGTGG | 600

```
CAGCAGGGGA ACGTCTTCTC ATGCTCCGTG ATGCATGAGG CTCTGCACAA CCACTACACG    660

CAGAAGAGCC TCTCCCTGTC TCCGGGTAAA TGA                                 693
```

( 2 ) INFORMATION FOR SEQ ID NO:4:

( i ) SEQUENCE CHARACTERISTICS:
        ( A ) LENGTH: 1231 base pairs
        ( B ) TYPE: nucleic acid
        ( C ) STRANDEDNESS: single
        ( D ) TOPOLOGY: unknown ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

```
CAACAACCAT GCTGGGCATC TGGACCCTCC TACCTCTGGT TCTTACGTCT GTTGCTAGAT     60

TATCGTCCAA AAGTGTTAAT GCCCAAGTGA CTGACATCAA CTCCAAGGGA TTGGAATTGA    120

GGAAGACTGT TACTACAGTT GAGACTCAGA ACTTGGAAGG CCTGCATCAT GATGGCCAAT    180

TCTGCCATAA GCCCTGTCCT CCAGGTGAAA GGAAAGCTAG GGACTGCACA GTCAATGGGG    240

ATGAACCAGA CTGCGTGCCC TGCCAAGAAG GGAAGGAGTA CACAGACAAA GCCCATTTTT    300

CTTCCAAATG CAGAAGATGT AGATTGTGTG ATGAAGGACA TGGCTTAGAA GTGGAAATAA    360

ACTGCACCCG GACCCAGAAT ACCAAGTGCA GATGTAAACC AAACTTTTTT TGTAACTCTA    420

CTGTATGTGA ACACTGTGAC CCTTGCACCA AATGTGAACA TGGAATCATC AAGGAATGCA    480

CACTCACCAG CAACACCAAG TGCAAAGAGG AAGGATCCAG ATCTTGTGAC AAAACTCACA    540

CATGCCCACC GTGCCCAGCA CCTGAACTCC TGGGGGGACC GTCAGTCTTC CTCTTCCCCC    600

CAAAACCCAA GGACACCCTC ATGATCTCCC GGACCCCTGA GGTCACATGC GTGGTGGTGG    660

ACGTGAGCCA CGAAGACCCT GAGGTCAAGT TCAACTGGTA CGTGGACGGC GTGGAGGTGC    720

ATAATGCCAA GACAAAGCCG CGGGAGGAGC AGTACAACAG CACGTACCGT GTGGTCAGCG    780

TCCTCACCGT CCTGCACCAG GACTGGCTGA ATGGCAAGGA GTACAAGTGC AAGGTCTCCA    840

ACAAAGCCCT CCCAGCCCCC ATCGAGAAAA CCATCTCCAA AGCCAAAGGG CAGCCCCGAG    900

AACCACAGGT GTACACCCTG CCCCCATCCC GGGAGGAGAT GACCAAGAAC CAGGTCAGCC    960

TGACCTGCCT GGTCAAAGGC TTCTATCCCA GCGACATCGC CGTGGAGTGG GAGAGCAATG   1020

GGCAGCCGGA GAACAACTAC AAGACCACGC CTCCCGTGCT GGACTCCGAC GGCTCCTTCT   1080

TCCTCTATAG CAAGCTCACC GTGGACAAGA GCAGGTGGCA GCAGGGGAAC GTCTTCTCAT   1140

GCTCCGTGAT GCATGAGGCT CTGCACAACC ACTACACGCA GAAGAGCCTC TCCCTGTCTC   1200

CGGGTAAATG AACTAGTTCT AGAGCGGCCG C                                  1231
```

HUMAN ANTI-FAS IGG1 MONOCLONAL ANTIBODIES

CROSS-REFERENCE TO RELATED APPLICATIONS

This application is a continuation-in-part of U.S. application Ser. No. 08/159,003, filed Nov. 29, 1993, now abandoned, which is a continuation-in-part of U.S. application Ser. No. 08/136,817, filed Oct. 14, 1993, now abandoned, entitled "Fas antagonists and uses thereof".

TECHNICAL FIELD

This invention is in the fields of molecular biology, biochemistry and immunology. Described herein are compositions that have prophylactic or therapeutic applications for the treatment of diseases :related to excess or otherwise unwanted programmed or activation-induced cell death. More specifically, materials that affect the interaction of Fas and Fas-ligand (Fas-L) and also can transduce signals through the Fas receptor are provided.

BACKGROUND OF THE INVENTION

During T cell development and regulation of immune responses, negative control mechanisms ensure that autoreactive or nonfunctional T cells are deleted and excessive expansion of peripheral T cells is prevented. Elimination of immature thymocytes and mature peripheral T cells occur via induction of programmed cell death, apoptosis, in which the cytoplasm of the affected cells condenses, the plasma membrane becomes convoluted, the nucleus condenses, and DNA fragmentation occurs. Prior art data suggest two pathways by which apoptosis of T cells may be induced. One pathway may involve stimulation of the CD3 T-cell receptor (TCR) complex. The other pathway may involve the cell surface Fas antigen. Fas is a member of the nerve growth factor/tumor necrosis factor receptor superfamily. Watanabe-Fukanaga et al. (*J. Immunol.* 148: 1274–79 (1992)) and Itoh et al. (*Cell* 66: 233–43 (1991)) have reported cloning of cDNA encoding murine and human Fas antigen, respectively.

Mice homozygous for the autosomal recessive mutation known as the lymphoproliferation (lpr) mutation have defects in the Fas antigen gene and do not express normal functional Fas protein capable of transducing the apoptotic signal (Watanabe-Fukunaga et al., *Nature* 356: 314–17 (1992)). These mice develop disorders characterized by the accumulation of $CD4^-$ $CD8^-$ T cells in lymph nodes and the spleen, hypergammaglobulinemia, autoantibody production, rheumatoid factor, arthritis and glomerulonephritis. Id.

Other mice homozygous for a mutant gene known as the generalized lymphoproliferative disease (gld) mutation exhibit a clinical syndrome indistinguishable from that found in lpr mice (J. B. Roths et al., *J. Exp. Med.,* 159: 1–20 (1984)). The gld gene maps to mouse chromosome 1 whereas lpr gene maps to mouse chromosome 19. Although the product of the gld gene has not been isolated., Allen et al. (*J. Exp. Med.,* 172: 1367–75 (1990)) have suggested that lpr and gld genes encode an interacting ligand-receptor pair of molecules expressed on different cells.

The Fas antigen was originally defined by two monoclonal antibodies, CH-11 and anti-APO-1. CH-11 belongs to the IgM class of immunoglobulins. Anti-APO-1 belongs to the IgG3 class of immunoglobulins. Both CH-11 and anti-APO-1 monoclonal antibodies bind to cells expressing human Fas, work as agonists, and induce apoptosis in lymphoid cell lines expressing Fas. Both CH-11 and anti-APO-1 antibodies were selected based upon their cytolytic activity towards certain in vitro cultured cell lines.

Monoclonal antibodies that block binding of CH-11 to cells expressing Fas antigen or that block CH-11-mediated or Fas-L-mediated lysis of lymphoid cell lines have not yet been disclosed. Such blocking antibodies would be useful, for example, in research applications to provide insight into its role in normal immune responses as well as in the generation of autoimmune diseases. Blocking antibodies also would be useful in therapeutic applications requiring inhibition of Fas- or Fas L-mediated biological activity.

The present invention provides such antibodies and other related advantages.

SUMMARY OF THE INVENTION

The present invention provides novel IgG1 monoclonal antibodies that specifically bind to the extracellular domain of human Fas and at about a 10-fold molar excess inhibit binding of anti-Fas monoclonal CH-11. to cells expressing Fas by about 4% to about 63%. The monoclonal antibodies are selected from the group consisting of murine and humanized monoclonal antibodies. Blocking studies show that many of these monoclonal antibodies block CH-11 monoclonal antibody-mediated lysis of Fas-expressing cells within a range of 10% to in excess of 90% at about a 1:1 to about a 10:1 molar ratio (molar ratio of IgG1 monoclonal antibody to CH-11). Some of these IgG1 Fas monoclonal antibodies were able to cause significant lysis of cell lines expressing the Fas antigen, but lysis was only observed when the antibodies were first bound to a solid-phase support. When the monoclonal antibodies were added in solution to cultures of cell lines expressing the Fas antigen less than 30% lysis of the cells was observed for any of the antibodies. In addition, certain of the Fas monoclonal antibodies stimulate the proliferation of T-cells independent of interleukin 2 when solid-phase bound. Within a related aspect of the invention, therapeutic compositions are provided comprising an IgG1 monoclonal antibody to Fas as described above and a physiologically acceptable carrier or diluent.

The present invention also provides novel IgG1 monoclonal antibodies that specifically bind to the extracellular domain of human Fas, stimulate the proliferation of T cells independent of interleukin 2, and block Fas ligand-mediated lysis of Fas-expressing cells by at least 10%. Within a related aspect of the invention, therapeutic compositions are provided comprising an IgG1 monoclonal antibody to Fas as described above and a physiologically acceptable carrier or diluent.

The invention further provides for a binding protein that specifically binds to a human Fas antigen comprising a Fas-binding domain encoded by a DNA sequence encoding an antibody or a portion thereof that specifically binds to the extracellular domain of human Fas antigen. The binding protein may also stimulate the proliferation of T cells independent of interleukin 2. Within a related aspect of the invention, a therapeutic composition is provided comprising a binding protein that specifically binds to human Fas antigen, and a physiologically acceptable carrier or diluent.

Further still, the invention provides for a therapeutic composition comprising a soluble fusion protein and a physiologically acceptable carrier or diluent. The soluble fusion protein, designated huFas/Fc, inhibits virtually all Fas-ligand-mediated lysis of lymphoid cells expressing Fas.

BRIEF DESCRIPTION OF THE DRAWINGS

FIG. 1A is representative of the results of six experiments in which peripheral blood T cells were cultured with immobilized huFas M33 and M38 monoclonal antibodies in the presence or absence of immobilized CD3 monoclonal antibody for 3 days and pulsed with $^3$H-TdR for the final 6 hours. FIG. 1B is representative of the results of three experiments in which thymocytes were cultured with immobilized huFas M38 monoclonal antibody in the presence or absence of immobilized CD3 monoclonal antibody for 3 days and pulsed with $^3$H-TdR for the final 6 hours. Data in FIGS. 1A and 1B represent mean ±SD of triplicate cultures.

In FIGS. 2A and 2B. T cells from peripheral blood were stimulated for 48 hours with either immobilized CD3 monoclonal antibody alone (FIG. 2A) or immobilized CD3 monoclonal antibody plus immobilized huFas M38 (FIG. 2B) and analyzed by 2-color flow cytometry using CD4-PE together with CD25-FITC. In FIGS. 2C and 2D, T cells were stimulated for 48 hours with immobilized CD3 monoclonal antibody alone (FIG. 2C) or immobilized CD3 monoclonal antibody plus immobilized huFas M38 (FIG. 2D) and analyzed by 2-color flow cytometry using CD4-PE together with CD69-FITC. In FIGS. 2E and 2F, T cells were stimulated for 48 hours with either immobilized CD3 monoclonal antibody alone (FIG. 2E) or immobilized CD3 monoclonal antibody plus immobilized huFas M38 (FIG. 2F) and analyzed by 2-color flow cytometry using CD8-PE together with CD25-FITC. In FIGS. 2B and 2H, T cells were stimulated for 48 hours with either immobilized CD3 monoclonal antibody alone (FIG. 2G) or immobilized CD3 monoclonal antibody plus immobilized huFas M38 (FIG. 2H) and analyzed by 2-color flow cytometry using CD8-PE together with CD69-FITC. Data in each figure are representative of three experiments performed.

In FIG. 3A, peripheral blood T cells were cultured for 72 hours with immobilized CD3 monoclonal antibody and IL-2. In FIG. 3B, peripheral blood T cells were cultured for 72 hours with immobilized CD3 monoclonal antibody and immobilized huFas M38 monoclonal antibody. In both FIGS. 3A and 3B, cells were cultured in the presence (filled circle) or absence (open circle) of a neutralizing IL-2 antiserum at a 1:500 dilution. Data in each figure are representative of four experiments performed.

FIG. 7A shows that Fas M3 monoclonal antibody substantially blocked apoptosis induced by PMA plus ionomycin in two different long-term cultured human $CD4^+$ T cell clones. TCC cultured in an antibody-free control medium are represented by stippled bars; in medium containing Fas M3 antibody alone are represented by diagonally-hatched bars; in medium containing PMA and ionomycin are represented by filled bars; and in medium containing PMA, ionomycin and Fas M3 antibody are represented by wavey-hatched bars. FIG. 7B shows that soluble huFas M3 monoclonal antibody (the diagonally-hatched center bar in each set of bar graphs) substantially blocked apoptosis in TCC induced by engaging the TCR/CD3 complex with OKT3 monoclonal antibody or by culturing TCC with PHA or PMA plus ionomycin. The antibody-free control is represented by stippled bars and an IgG1 monoclonal antibody control is represented by a filled bar on the right in each set of bar graphs. FIG. 7C shows that the Fas/Fc fusion protein blocked activation-induced apoptosis in TCC similar to huFas M3 monoclonal antibody whereas as a control IgG1 immunoglobulin had no effect. The control is represented by the stippled bar on the far left; the IgG1 immunoglobulin results are represented by the second (diagonally-hatched) bar from the left, the Fas M3 results are represented by the third (filled) bar and huFas/Fc fusion protein results are represented by the fourth (wavey-hatched) bar from the left in each set of bar graphs.

DETAILED DESCRIPTION OF THE INVENTION

Figure 1A:
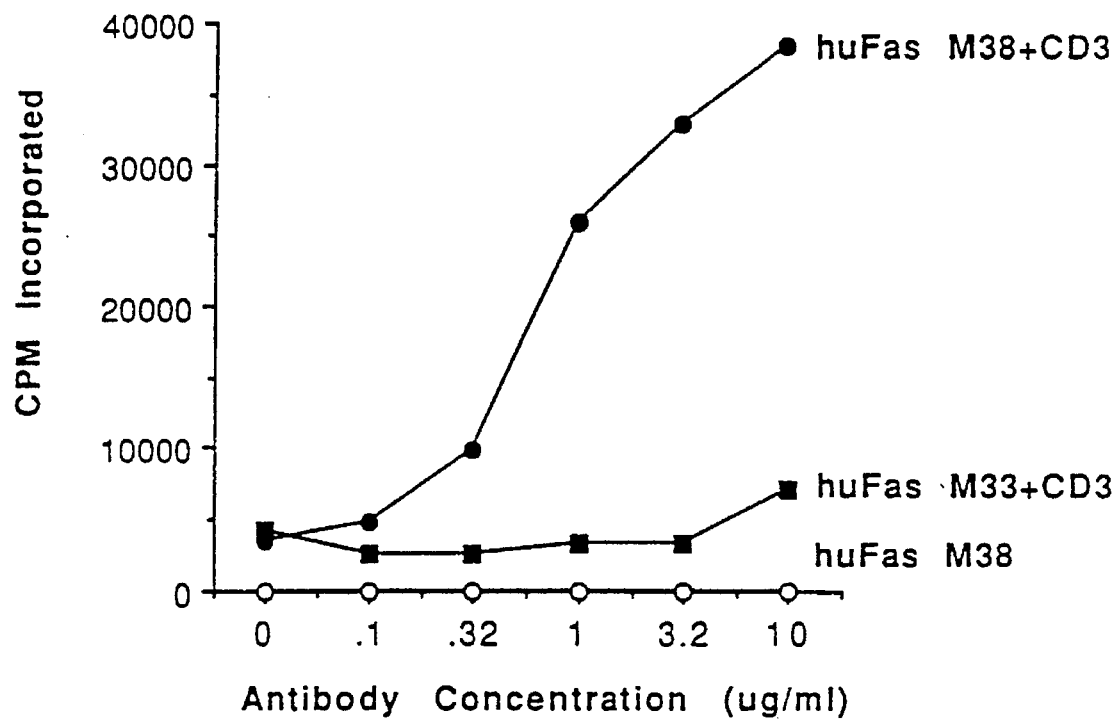
FIGS. 1A and 1B show the costimulation potential of T cell proliferation by huFas M38 monoclonal antibody with CD3 monoclonal antibody (filled circles) and without CD3 monoclonal antibody (open circles) and huFas M33 with CD3 monoclonal antibody (filled squares).

The antigen Fas (also termed APO-1) is a member of the nerve growth factor/tumor necrosis factor receptor superfamily. In the past, conclusions about the function of Fas were made based upon in vitro data generated with the two original monoclonal antibodies (clone CH-11 and anti-APO-1) that were selected based upon their cytolytic activity towards certain cell lines. Data associated with the present invention shows the existence of a complex set of interactions mediated by Fas and that Fas plays a role in the induction of apoptosis in certain transformed cell lines and the activation and proliferation of normal T cells.

In accordance with the present invention, we developed a panel of Fas monoclonal antibodies based upon their ability to simply bind huFas and thus generated monoclonal antibodies with a variety of biological properties. The panel of monoclonal antibodies generated against huFas were characterized in terms of (1) their ability to inhibit binding of CH-11 to cells expressing Fas; (2) their ability to kill cell lines expressing Fas when added in solution or when bound to culture plates; and (3) their ability to inhibit CH-11-induced or Fas-ligand (Fas-L)-induced apoptosis in lymphoid cell lines expressing Fas. In addition, the effects of these huFas-specific antibodies on freshly isolated human T lymphocytes that could be induced to express Fas were examined.

A huFas cDNA was cloned and the DNA and encoded amino acid sequences reported by Itoh et al. (*Cell* 66: 233–43 (1991)). Purified Fas antigen may be utilized to prepare monoclonal antibodies, as well as other binding proteins that may be specifically constructed utilizing recombinant DNA methods. These binding proteins may incorporate the variable regions of a specifically binding monoclonal antibody.

As will be evident to one of ordinary skill in the art, antibodies may be generated against either whole Fas antigen, or portions of the Fas antigen. Particularly preferred are antibodies developed against the soluble form of the human Fas antigen. Additionally, within the context of the present invention, binding proteins and monoclonal antibodies include antigen-binding fragments, e.g., F(ab')$_2$ and Fab fragments, that may be readily prepared by one of ordinary skill in the art.

Monoclonal antibodies (mAbs) may also be readily generated using conventional techniques (see U.S. Pat. Nos. RE 32,011, 4,902,614, 4,543,439, and 4,411,993 which are incorporated herein by reference; see also *Monoclonal Antibodies, Hybridomas: A New Dimension in Biological Analyses*, Kennett et al (eds.), Plenum Press (1980); and *Antibodies. A Laboratory Manual*, Harlow and Lane (eds.), Cold Spring Harbor Laboratory Press (1988), which also are incorporated herein by reference). Other techniques that enable the production of antibodies through recombinant techniques (e.g., techniques described by William D. Huse et al., *Science*, 246: 1275–1281 (1989); L. Sastry et al., *Proc. Natl. Acad. Sci. USA*, 86: 5728–5732 (1989); and Michelle Alting-Mees et al., *Strategies in Molecular Biology*, 3: 1–9 (1990) involving a commercial system available from Stratacyte, La Jolla, Calif.) may also be utilized to construct monoclonal antibodies.

Similarly, binding proteins may also be constructed utilizing recombinant DNA techniques to incorporate the portion of a gene that encodes the variable region of a specifically binding antibody. The construction of these proteins may be readily accomplished by one of ordinary skill in the art (see James W. Larrick et al., *Biotechnology*, 7: 934–938 (1989); Riechmann et al., *Nature (England)* 332: 323–327 (1988); Roberts et al., *Nature (England)* 328: 731–734 (1987); Verhoeyen et al., *Science* 239: 1534–1536 (1988); Chaudhary et al., *Nature (England)* 339: 394–397 (1989)) given the disclosure provided herein. Briefly, DNA encoding the antigen-binding sites or Fas antigen binding domain of a specifically binding monoclonal antibody is amplified, and inserted directly into the genome of a cell which produces human antibodies (see Verhoeyen et al., supra; see also Reichmann et al., supra). This technique allows the antigen-binding site of a specifically binding murine (mouse or rat) monoclonal antibody to be transferred into a human antibody. Such antibodies are preferable for therapeutic use in humans because they are not as antigenic as rat or mouse antibodies. Alternatively, the antigen-binding sites (variable region) may be either linked to, or inserted into, another completely different protein (see Chaudhary et al., supra), resulting in a new protein with antigen-binding sites of the antibody as well as the functional activity of the completely different protein. As one of ordinary skill in the art will recognize, the antigen-binding sites or Fas antigen binding domain of the antibody may be found in the variable region of the antibody. Furthermore, DNA sequences which encode smaller portions of the antibody or variable regions which specifically bind to mammalian Fas antigen may also be utilized within the context of the present invention. These portions may be readily tested for binding specificity to the Fas antigen utilizing assays, including for example ELISA, ABC, or dot blot assays.

Thus, the present invention provides humanized monoclonal antibodies derived from the murine monoclonal antibodies listed in Table 1. Other embodiments of the invention are directed to recombinant binding proteins that comprise an antigen-binding site of a monoclonal antibody listed in Table 1, wherein the binding proteins comprise an amino acid sequence that has been altered (compared to the native sequence of the MAb of Table 1), or wherein the binding protein is a fusion protein comprising additional polypeptide sequence(s) derived from a protein other than a MAb of Table 1.

The humanized antibodies preferably comprise the constant region of a human antibody that is of an isotype equivalent to that of the murine antibody from which the antigen binding site is derived. The murine monoclonal antibodies of Table 1 are of subclass IgG1. The human immunoglobulin subclass IgG4 is equivalent to murine immunoglobulin subclass IgG1 (Golub, Edward, *Immunology. A Synthesis*, Sinauer Assocs., Inc., Sunderland, Mass., 1987, at page 58).

Regarding binding proteins comprising the antigen-binding site of a monoclonal antibody fused to a non-immunoglobulin-derived polypeptide, one example is an enzyme detectable in assays, fused to said antigen-binding site. Such a fusion protein finds use in assays for cells expressing Fas antigen, for example. In another example, the non-immunoglobulin derived polypeptide is a protein toxin, such that the fusion protein has a cytotoxic effect on Fas-bearing cells.

Other binding proteins include engineered antibodies derived from the antibodies of Table 1 by known techniques. (See Roberts et al., supra, and Riechmann et al., supra, for example.) In addition, the amino acid sequence of a polypeptide derived from a monoclonal antibody disclosed herein may be altered by such techniques as site-directed mutagenesis, and antibodies comprising the mutant polypeptides may be screened for desired biological properties.

The above-described humanized MAbs and binding proteins may comprise the entire variable region of a MAb of Table 1, or a fragment of said variable region that includes the antigen-binding site. cDNA encoding the variable region or fragment thereof may be prepared from mRNA isolated from a hybridoma cell line of the present invention. The cDNA may be rinsed to DNA encoding a human antibody constant region, or to DNA encoding a non-immunoglobulin polypeptide. Appropriate host cells transfected with an expression vector containing the gene fusion are cultured to produce the encoded recombinant protein.

Larrick et al., supra, describe a general method for isolating DNA encoding the variable region of any immunoglobulin chain. The method involves a polymerase chain reaction, employing a mixture of upstream primers corresponding to the leader sequence, and a downstream primer based on the conserved sequence of the constant region. If desired, the isolated DNA may be fused to DNA encoding a particular constant region polypeptide, e.g., the constant region of a human antibody.

In the instant invention, a cDNA fragment encoding the extracellular region (ligand binding domain) of huFas was obtained using polymerase chain reaction (PCR) techniques and coupled to the constant region of human IgG1 antibody to form a soluble huFas/Fc fusion protein. As described more fully below in Example 1, DNA encoding the extracellular domain of huFas was amplified by PCR using DNA synthesized from RNA isolated from a human T-cell hybridoma as a template. Primers used in the PCR were based on the huFas sequence published by Itoh et al. supra. An expression vector comprising the huFas extracellular domain DNA fused in-frame to the 5'-terminus of human IgG1 Fc region DNA sequence was constructed and transfected into mammalian cells. The expressed protein was purified by a procedure that involved the Fc portion of the fusion protein binding to protein G in an affinity column. The soluble huFas/Fc fusion protein was used (1) to generate anti-huFas monoclonal antibodies described in the examples below, (2) to assess the fusion protein's ability to inhibit the lysis of Fas-expressing target cells mediated by cells expressing Fas-L, and (3) to assess the fusion protein's ability to interfere with activation-induced apoptosis (AIA) in lymphoid cell lines expressing Fas.

To generate anti-huFas monoclonal antibodies, BALB/cJ mice were immunized with the huFas/Fc fusion protein in Freund's adjuvant as described in Example 2. Spleen cells from the mice were fused with a murine myeloma to form hybridomas. Hybridomas that produce monoclonal antibodies positive for binding to huFas/Fc but not to human IgG1 were cloned. All the monoclonal antibodies from the cloned hybridomas were determined to be of the IgG1 isotype and were purified by protein A affinity chromatography. The hybridoma clone huFas M38 generated according to the above procedure and producing huFas M38 monoclonal antibodies has been deposited on Oct. 19, 1993, with the American Type Culture Collection (ATCC), 12301 Parklawn Drive, Rockville, Md. 20852, USA (Accession No. HB 11465). The hybridoma cell line huFasM3, which produces huFasM3 monoclonal antibodies, was deposited with ATCC on Oct. 11, 1994, and assigned accession no. HB11726. Both deposits were made under the conditions of the Budapest Treaty. The present invention provides monoclonal antibodies M38 and M3, which are produced by the deposited hybridoma cell lines, as well as monoclonal antibodies having the biological characteristics of M38 or M3. Certain characterizing biological properties of M38 and M3 are presented in Table 1.

Once suitable antibodies or binding proteins have been obtained, they may be isolated or purified by many techniques well known to those of ordinary skill in the art. See e.g., *Antibodies. A Laboratory Manual,* Harlow and Lane (eds.), Cold Spring Harbor Laboratory Press (1988). Suitable techniques include peptide or protein affinity columns, HPLC or RP-HPLC, purification on protein A or protein G columns, or any combination of these techniques.

In characterizing the IgG1 isotype Fas monoclonal antibodies, flow cytometry was used to assess their ability to block the binding of the CH-11 Fas monoclonal antibody to MP-1 cells. As described in Example 3, Fas bearing target cells were incubated with a blocking solution and then incubated with a test IgG1 Fas monoclonal antibody. The CH-11 monoclonal antibody was then added and incubated. The cells were washed twice with FACS buffer and incubated with an anti-mouse IgM-FITC (Tago) which has no cross-reactivity with mouse IgG1 to detect bound CH-11 antibody. Flow cytometry was then performed using a FACScan (Becton-Dickinson) and data were collected. The monoclonal antibodies varied in their ability to block CH-11 binding from less than 5% up to about 63% inhibition (Table 1).

Since the data from Example 3 for CH-11 binding suggest that many of IgG1 Fas monoclonal antibodies bound to a similar Fas epitope as CH-11, their ability to promote lysis of either Jurkat or MP-1 cells was tested. Jurkat and MP-1 cell lines are lysed by the CH-11 monoclonal antibody. The Fc domain of the Fas-specific monoclonal antibody APO-1 has been shown to profoundly affect its apoptotic efficacy (Dhein et al., *J. Immunol.,* 149: 3166–73 (1992)). In this regard, IgG1 isotype switch variants of APO-1 were relatively poor inducers of apoptosis unless cross-linked. Given that all of the huFas-specific monoclonal antibodies in Table 1 were of the IgG1 isotype, their ability to induce apoptosis in Jurkat and MP-1 target cells when added in solution and when cross-linked, i.e., bound to the plastic of the tissue culture plates, was assessed. As described in Example 4, an overnight $^{51}$Cr-release assay was used to measure cell lysis induced by huFas monoclonal antibodies. The ability to induce apoptosis in Fas bearing target cells was determined for the IgG1 isotype Fas monoclonal antibodies when the antibodies were added in solution and when crosslinked, i.e., bound to the plastic of tissue culture plates. The data collected are summarized in Table 1. Some of the IgG1 isotype Fas monoclonal antibodies (M23, M31, M33, and M35) have no cytolytic potential either in solution or when immobilized. Others (M1, M3, M24, and M38) were not cytolytic in solution but were at least slightly cytolytic when immobilized. Only one antibody, M2, was both slightly cytolytic in solution (less than 20% lysis) and cytolytic when immobilized.

The cytolysis studies were extended to determine whether some of the IgG1 isotype Fas monoclonal antibodies that induced apoptosis when immobilized were inhibitory to the cytolytic process induced by CH-11 when added in solution. Using a blocking assay described in Example 5, serial dilutions of IgG1 Fas antibodies with $^{51}$Cr-labeled Jurkat cells and a constant concentration of CH-11 known to lyse the Jurkat cells were incubated overnight and assayed for $^{51}$Cr-release from lysed cells using a overnight $^{51}$Cr-release assay. The cytolysis results are presented in Table 1. The results show that, consistent with their ability to cause partial blocking of CH-11 binding to Fas expressing cells, several monoclonal antibodies inhibited CH-11-mediated cell lysis. On the other hand, huFas M38 monoclonal antibody failed to block binding of CH-11 but it efficiently inhibited CH-11-induced target cell lysis. Thus, huFas M38 appears to inhibit CH-11-mediated apoptosis of target cells by binding to an epitope that is not recognized by the CH-11 antibody.

The cytolysis results also show that the M31 and M33 monoclonal antibodies bind to cell surface Fas yet neither induce nor inhibit apoptosis. They, therefore, presumably recognize epitopes not involved in signal transduction. Further, the M23 and M33 antibodies mediate substantial blocking of CH-11 binding to cell surface Fas, yet do not mediate lysis of Fas-expressing targets in either soluble or immobilized forms. Nor did they inhibit lysis of targets mediated by CH-11. Thus, binding to an epitope similar to that recognized by CH-11 is not predictive of whether an antibody will either mediate apoptosis directly or inhibit CH-11-mediated apoptosis.

Monoclonal antibody huFas M3 was strongly lytic when immobilized, failed to lyse cells when added in solution, and inhibited cell lysis induced by the CH-11 monoclonal antibody. This shows that huFas M3 can act as a CH-11 agonist when bound to plastic but as an antagonist when added in a soluble form. Antibodies that display antagonistic properties in solution have the potential to be extremely useful in determining the function of Fas in a normal immune response.

Flow cytometry and two-color staining techniques described in Example 6 were used to assess Fas monoclonal antibodies' ability to bind to T lymphocytes. Although specific binding to neutrophils, monocytes, SAC-activated B cells and PHA-induced T-cell blasts was detected, none of these cell types was induced to undergo cytolysis when cultured with either soluble or immobilized huFas monoclonal antibodies in the overnight $^{51}$Cr-release assay described in Example 2. These results support recently published data demonstrating strong expression of Fas by PHA blasts, but no adverse effect on cell viability upon exposure to huFas monoclonal antibodies. T. Miyawaki et al., *J. Immunol.*, 149: 3753–58 (1992).

Given that monoclonal antibodies against CD27, another member of the NGFR/TNFR family, have been shown to costimulate T-cell proliferation (R. A. W. Van Lier et al., *J. Immunol.*, 139: 1589–96 (1987)), a T cell costimulation assay was used to determine whether immobilized IgG1 isotype huFas monoclonal antibodies would costimulate T cells in conjunction with solid-phase CD3 monoclonal antibody. To do this a T cell costimulation assay described in Example 6 was used. The results obtained using the complete panel of huFas monoclonal antibodies are summarized in Table 1. Some, but not all, of the IgG1 isotype huFas monoclonal antibodies were found to be strong costimulators of T-cell proliferation with activity equivalent to, or greater than, that of IL-2. For example, huFas M38 costimulated T cell proliferation at concentrations as low as 100 ng/ml (FIG. 1). The huFas monoclonal antibodies, including CH-11, costimulated T cells only when immobilized and not when added to cultures in solution. For most of the IgG1 isotype Fas monoclonal antibodies, the ability to induce lysis of Fas-expressing cell lines correlated with their costimulatory activity on T cells. However, huFas M35 and M38 were potent costimulators of T-cell proliferation, but had little or no activity in the cytolysis assays. In contrast, the CH-11 monoclonal antibody lyses Jurkat and MP-1 targets when added in solution and yet can only costimulate T cells with CD3 monoclonal antibody when immobilized on the culture well.

Figure 1B:
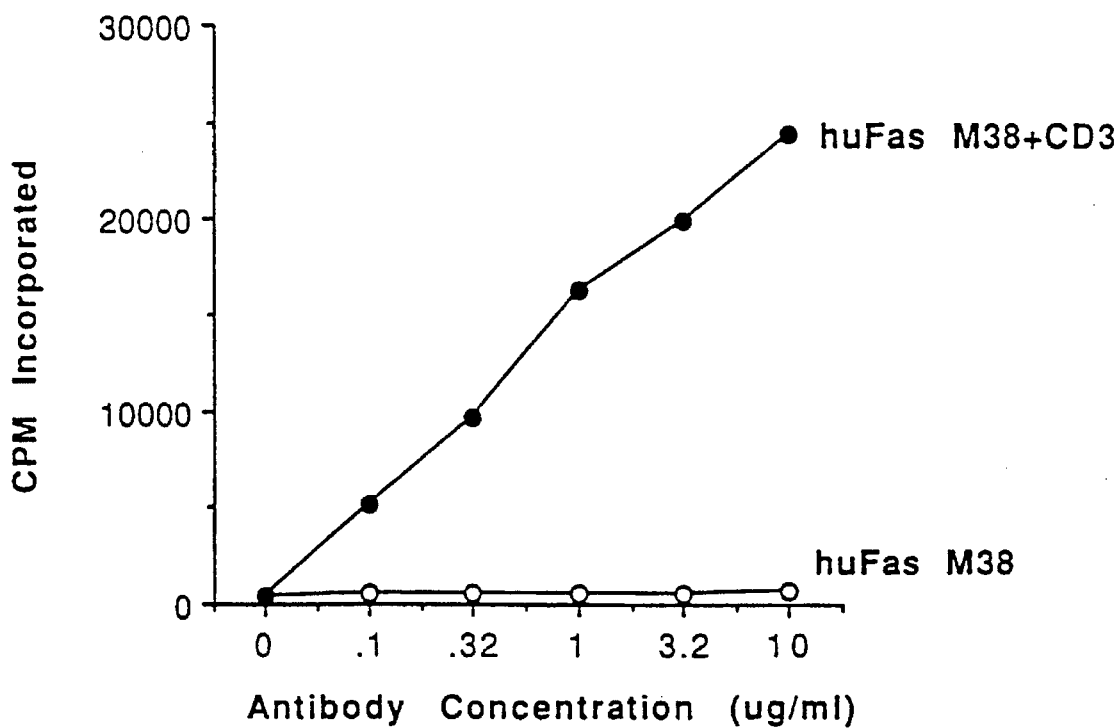
Figure 2A:
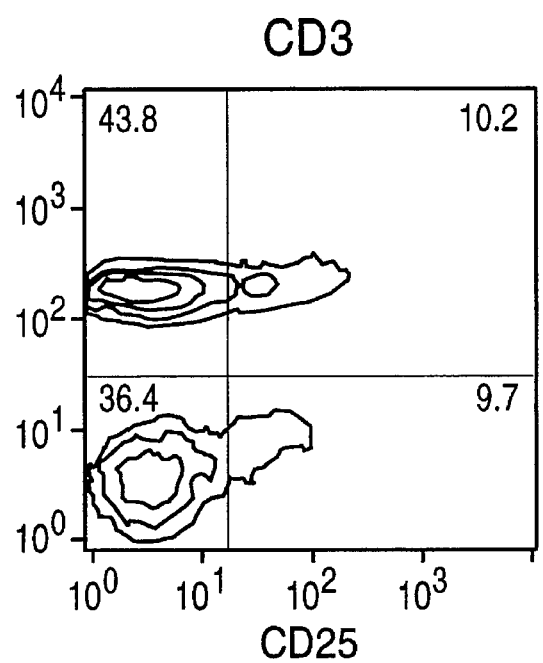
FIGS. 2A through 2H show that costimulation with huFas M38 enhances CD25 and CD69 expression by $CD4^+$ and $CD8^+$ T cells.
Figure 2B:
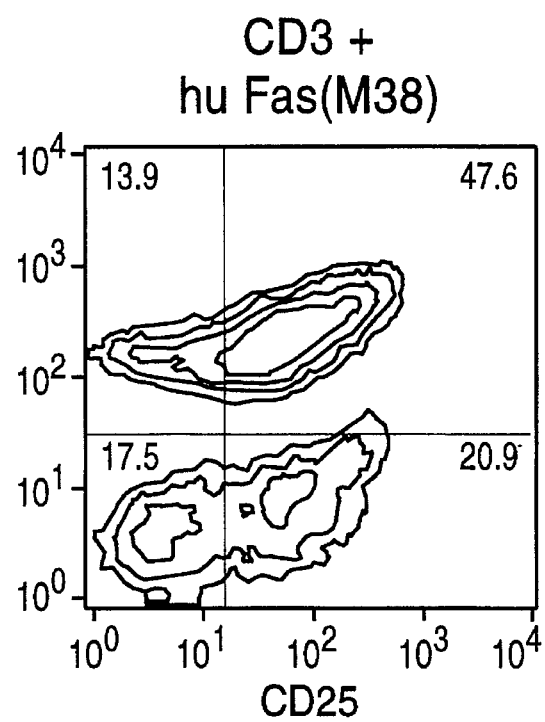
Figure 2C:
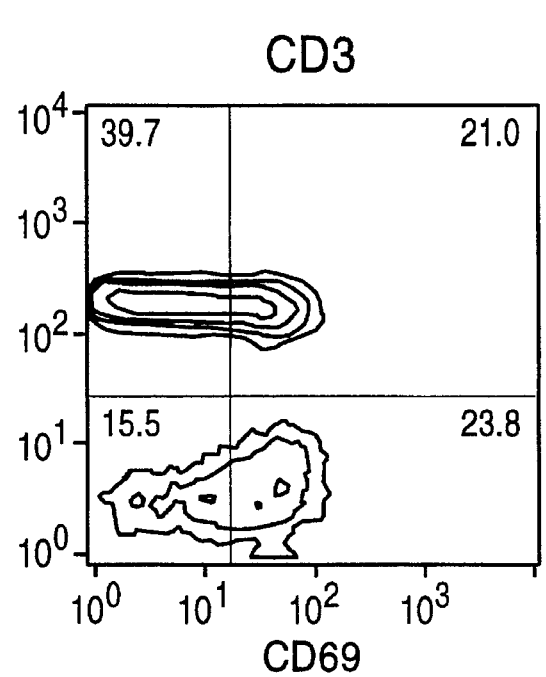
Figure 2D:
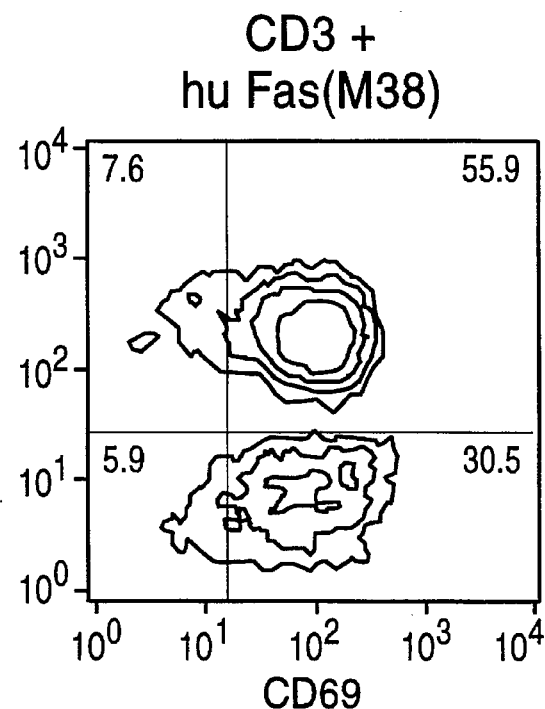
Figure 2E:
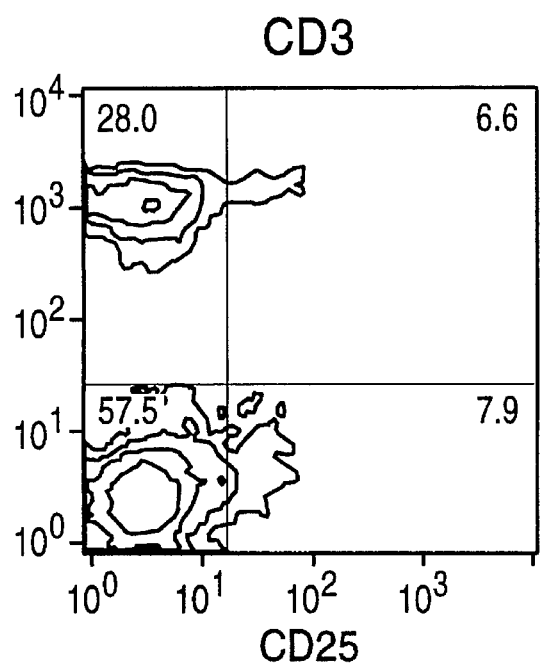
Figure 2F:
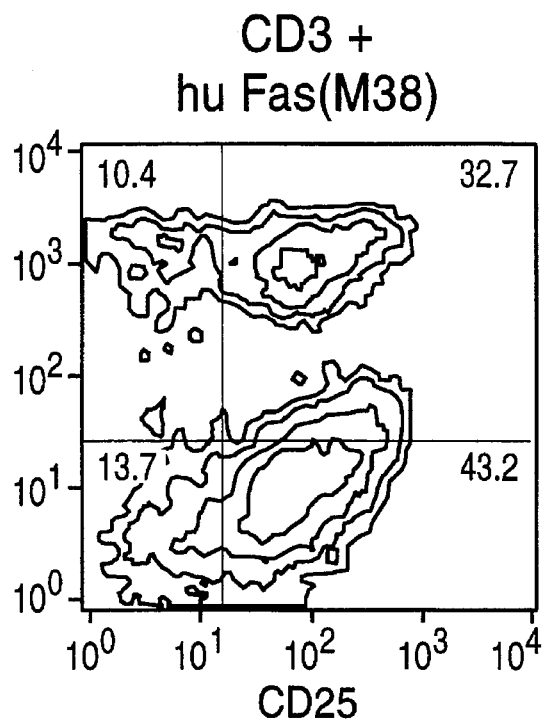
Figure 2G:
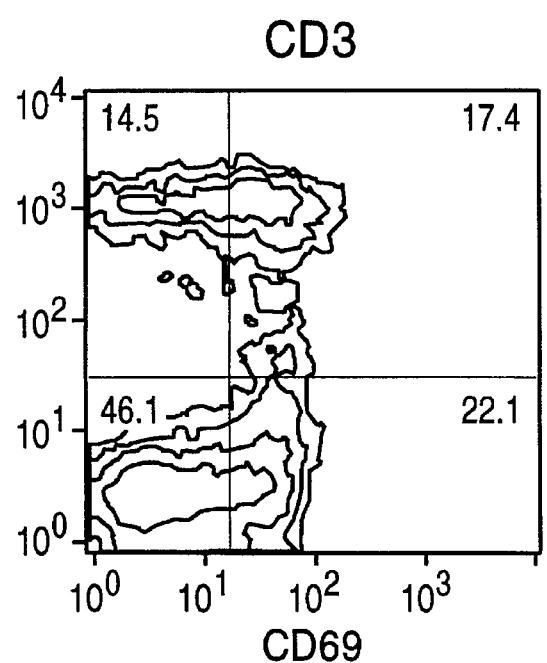
Figure 2H:
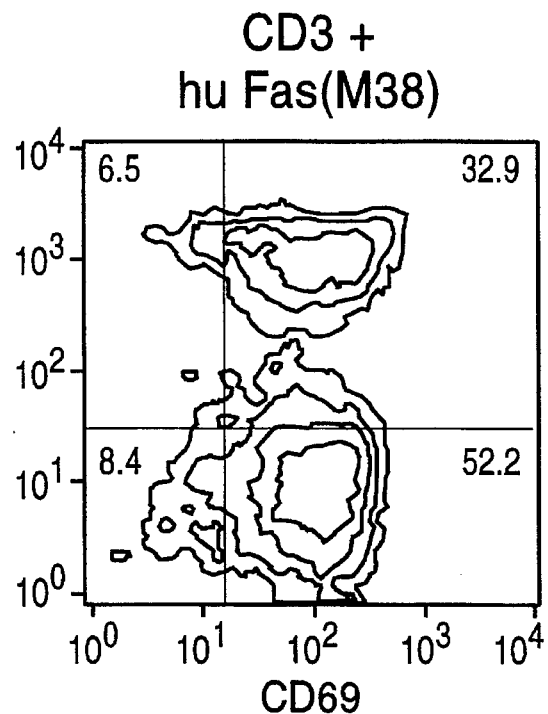

Given that thymocytes express Fas, thymocytes were tested for their ability to be costimulated using the procedure outlined above for peripheral blood T cells. Although results of E. Rouvier et al., *J. Exp. Med*, 177: 195–200 (1993) suggest that Fas can mediate lysis of normal murine thymocytes in a 4 hour $^{51}$Cr-release assay, here human thymocytes were costimulated to proliferate by immobilized huFas M38 monoclonal antibody in the presence of CD3 monoclonal antibody (FIG. 1B). Thus, it is possible that subsets of thymocytes may respond differentially to signals mediated by Fas.

To analyze the effect of Fas monoclonal antibodies on human T cells in more detail, flow cytometry and the T cell costimulation assay as described herein were used to determine whether the costimulation of peripheral blood T cells by huFas monoclonal antibodies was accompanied by enhanced expression of T-cell activation molecules. Two such molecules, the early activation antigen CD69 and the p55 low affinity chain of the IL-2 receptor CD25, were strongly enhanced on peripheral blood T cells stimulated with huFas M38 plus CD3 monoclonal antibody compared to CD3 monoclonal antibody alone (FIGS. 2A–2H). Two-color staining of cultured T cells, and flow cytometry methods described in Example 7 showed that huFas M38 enhanced expression of CD25 and CD69 was detected on both CD4$^+$ and CD8$^+$ T cells. Ligation of Fas by immobilized huFas M38 in the presence of CD3 monoclonal antibody also induced modest increases in expression of the adhesion molecules CD11a (LFA-1), CD18 and CD54 (ICAM-1).

Cytokine assays described in Example 7 were conducted. When combined with CD3 monoclonal antibody, some of the huFas monoclonal antibodies are able to costimulate T cells (Table 1) and do so independent of IL-2. The T cell costimulation and cytokine assays described above and in Examples 6 and 7 show that Fas is not only capable of inducing apoptosis in certain transformed cell lines, but can also be involved in the costimulation of freshly isolated T cells. For most of the IgG1 isotype Fas monoclonal antibodies, the ability to induce lysis of Fas-expressing cell lines correlated with their costimulatory activity on T cells. However, huFas M35 and M38 were potent costimulators of T-cell proliferation, but had little or no activity in the cytolysis assays. Data showed that the CH-11 monoclonal antibody could lyse Jurkat and MP-1 targets when added in solution and yet could only costimulate T cells with CD3 monoclonal antibody when immobilized on the culture well. Collectively these data suggest that the signals regulating the activation and apoptotic pathways mediated by Fas may be quite distinct or may involve different signaling sensitivities.

The results reported for M38 in example 7 are believed to be equally applicable to the other antibodies that are capable of costimulating proliferation of T-cells. Thus, monoclonal antibodies M1, M2, M3, M23, M24, M35, and M38 are believed to costimulate proliferation of T-cells in the presence of immobilized CD3 monoclonal antibody, independent of IL-2.

Figure 4:
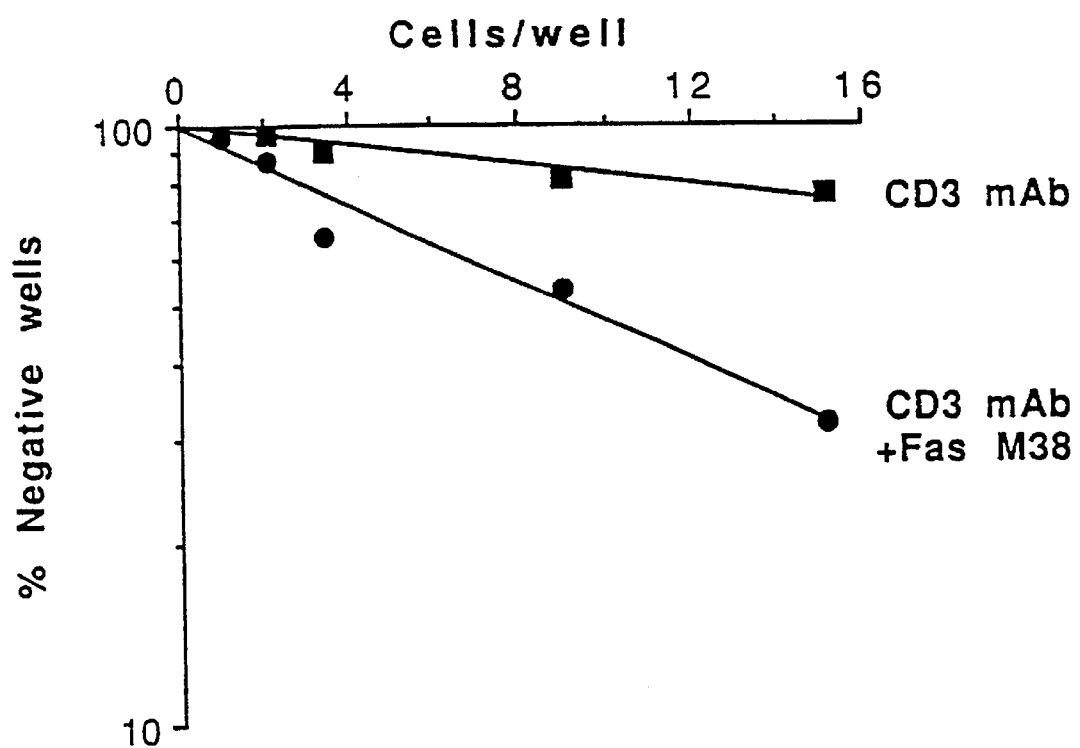
FIG. 4 shows the effect of huFas M38 on the frequency of proliferating T cell precursors. Graded numbers of purified T cells were cultured in 15 μl volumes in wells pre-coated with either CD3 monoclonal antibody alone (filled square) or CD3 monoclonal antibody plus huFas M38 monoclonal antibody (filled circle) in medium containing 10 ng/ml of IL-2. After 5 days the wells were scored microscopically for proliferating T-cell clones.

A limiting dilution analysis described in Example 8 was used to determine whether T cells were the direct target of action of Fas monoclonal antibodies in T-cell activation or whether interactions with accessory cells were required. A linear relationship between the number of input cells and the log of the percent negative wells (FIG. 4) suggests that the precursor T cells were the limiting component in the T cell cultures. The huFas M38 monoclonal antibody significantly enhanced the frequency of T cells stimulated to proliferate by immobilized CD3 monoclonal antibodies (Table 3). The data show that the Fas M38 monoclonal antibody has a direct costimulatory effect on T cells that does not require the involvement of accessory cells or other cell types. In addition, the data suggest that the effects of huFas M38 monoclonal antibody observed in high density cultures represent an increase in the frequency of responding T cells as well as increase in T-cell clone size.

Using a highly sensitive three-step flow cytofluorometric assay described in Example 9, the Fas/Fc fusion protein prepared according to Example 1 herein was found to specifically bind to the surface of an anti-tumor CTL line (B10 anti-B10.5) subsequent to stimulation with PMA and ionomycin. Supportive evidence that the determinant detected using this binding assay is Fas-L is provided by the fact that activated cells mediated lysis of target cells expressing the Fas cell surface receptor and that this lysis is completely inhibited by neutralizing huFas monoclonal antibodies (Table 1 and Example 10). For example, huFas-specific M3 monoclonal antibody not only abrogated Fas-mediated target cell lysis by the prototypic CH-11 monoclonal antibody, but also completely inhibited lysis of Jurkat target cells by the PMA and ionomycin stimulated B10 anti-B10.5 cells. Also, the characteristic DNA laddering pattern associated with the apoptosis process was induced by the activated B10 anti-B10.5 cells and was also completely abrogated by addition of the huFas M3 monoclonal antibodies to the bioassay. Because the huFas M3 monoclonal antibody binds to the target cells expressing Fas and not the effector cells expressing Fas-L, the possibility that the monoclonal antibody is non-specifically inhibiting expression of a cytotoxic activity of the B10 anti-B10.5 cells that functions via a non-Fas receptor mediated pathway is ruled out. Monoclonal antibodies directed to other antigens expressed by the target cells had no effect on the apoptosis of Jurkat target cells mediated by the activated CTL.

In addition, anti-huFas monoclonal antibodies that did not inhibit target cell lysis by the CH-11 antibody (such as huFas M31) also failed to inhibit lysis by the activated B10 anti-B10.5 cells, thereby demonstrating the epitope specificity of the inhibitory effect of these monoclonal antibodies. Finally, the huFas/Fc fusion protein, but not fusion proteins of other cell surface receptors, also inhibited lysis of Jurkat target cells by the activated B10 anti-B10.5 cells, presumably by competitively binding to the active site on the Fas-L that would otherwise interact with cell surface Fas and mediate target cell apoptosis. The possibility that the lysis of these target cells was caused by either cell-surface or soluble TNF is not supported since both Jurkat and MP-1 target cells have been found to be completely resistant to TNF-mediated killing at concentrations as high as 100 ng/ml. Fas-L is rapidly induced and synthesized following stimulation of an antigen-specific T cell line, but appears to be only transiently expressed on the cell surface.

Figure 7A:
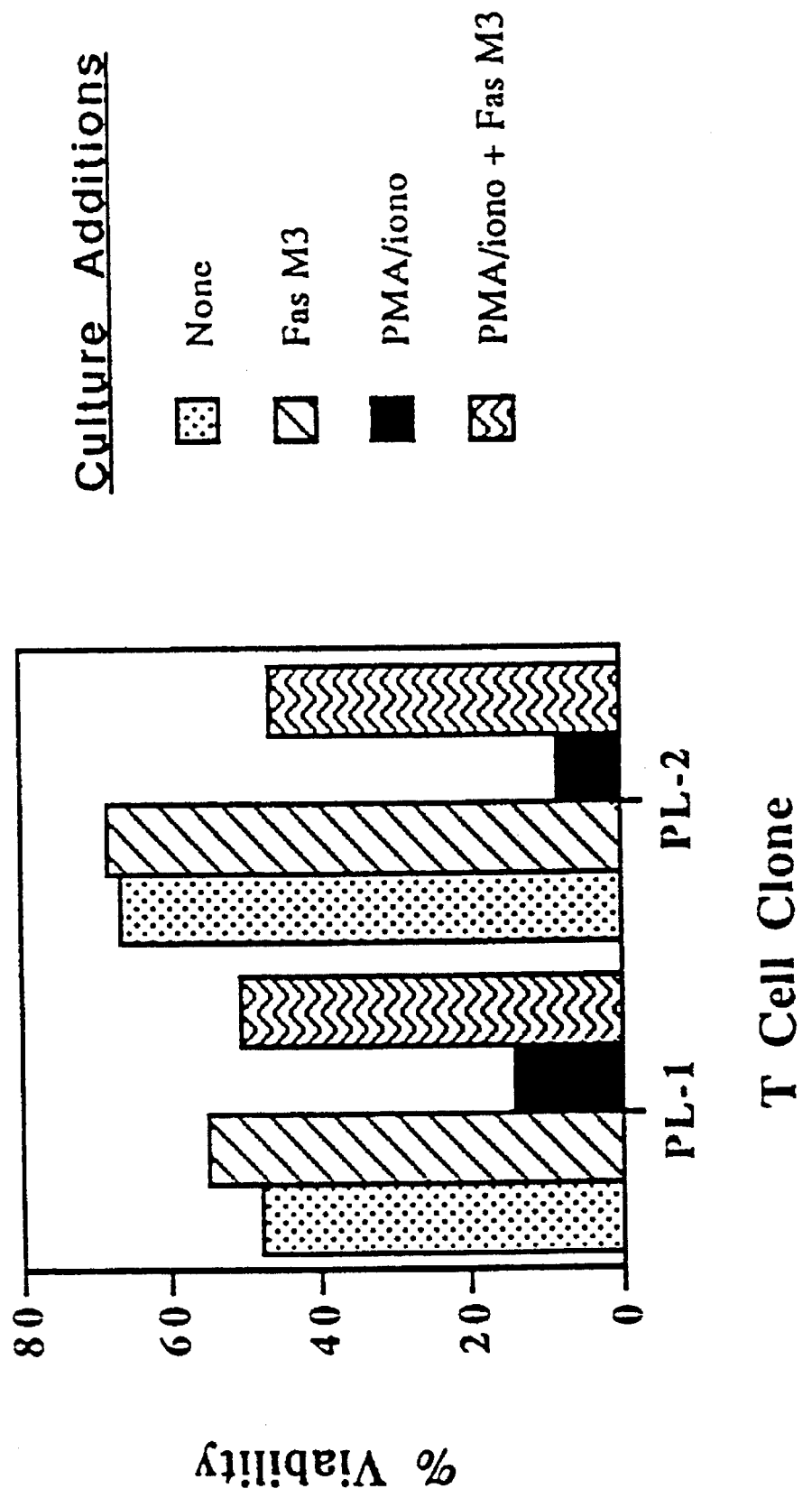
FIGS. 7A, 7B and 7C show that Fas antagonists inhibit activation induced apoptosis in long-term cultured human $CD4^+$ T cell clones (TCC).

To address whether activation-induced apoptosis and apoptosis induced by cross-linking Fas may be causally related, antagonists of Fas were used in an attempt to block apoptosis induced by stimulating long-term cultured human $CD4^+$ T cell clones (TCC) with phorbol ester (PMA) and calcium ionophore (ionomycin). Cell viability was determined by trypan blue dye exclusion as described in Example 11. A significant decrease in cell viability was observed in TCC cultured in medium containing PMA plus ionomycin when compared to TCC cultured in medium alone or medium containing Fas M3 monoclonal antibody. This effect was completely inhibited by addition of FasM3 monoclonal antibody to TCC cultured in medium containing PMA plus ionomycin (FIG. 7A).

Figure 7B:
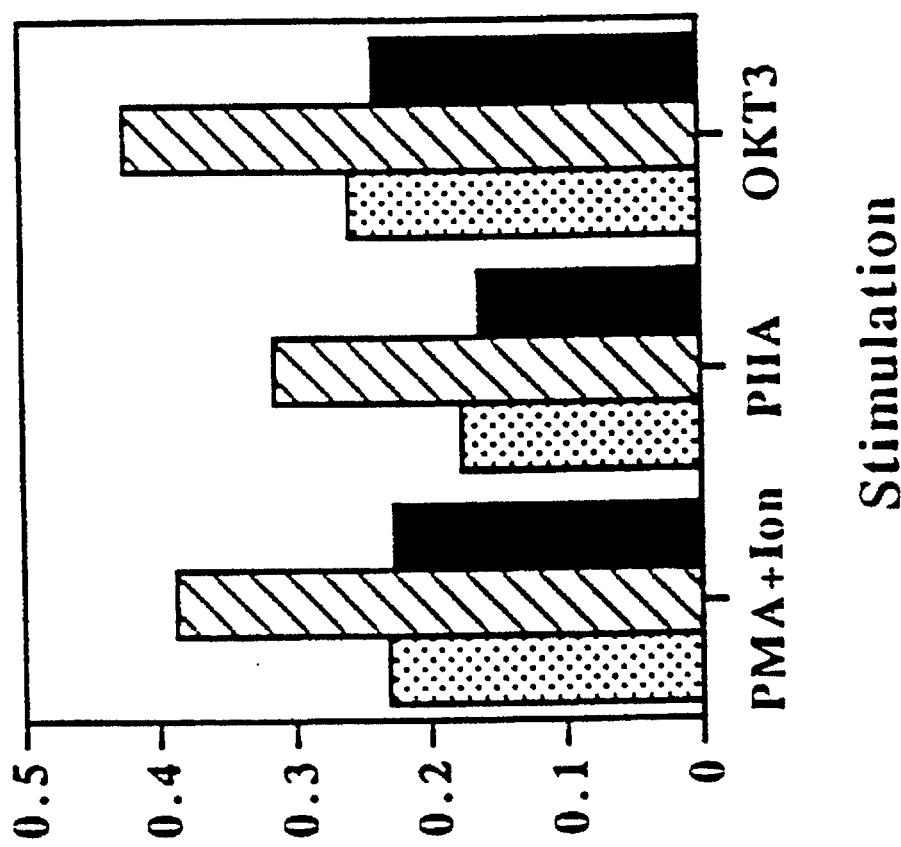

In a follow-up experiment, apoptosis was induced by engaging the TCR/CD3 complex or by culturing TCC with PHA or PMA plus ionomycin. An MTT colorimetric assay described in Example 11 was used to detect differences in MTT conversion in TCC cultured in medium alone, medium with Fas M3 antibody, and medium with IgG1 immunoglobulin. Soluble Fas M3 monoclonal antibody substantially blocked apoptosis in TCC induced by any one of the three stimuli tested, whereas addition of a control IgG1 immunoglobulin had no effect (FIG. 7B).

Figure 7C:
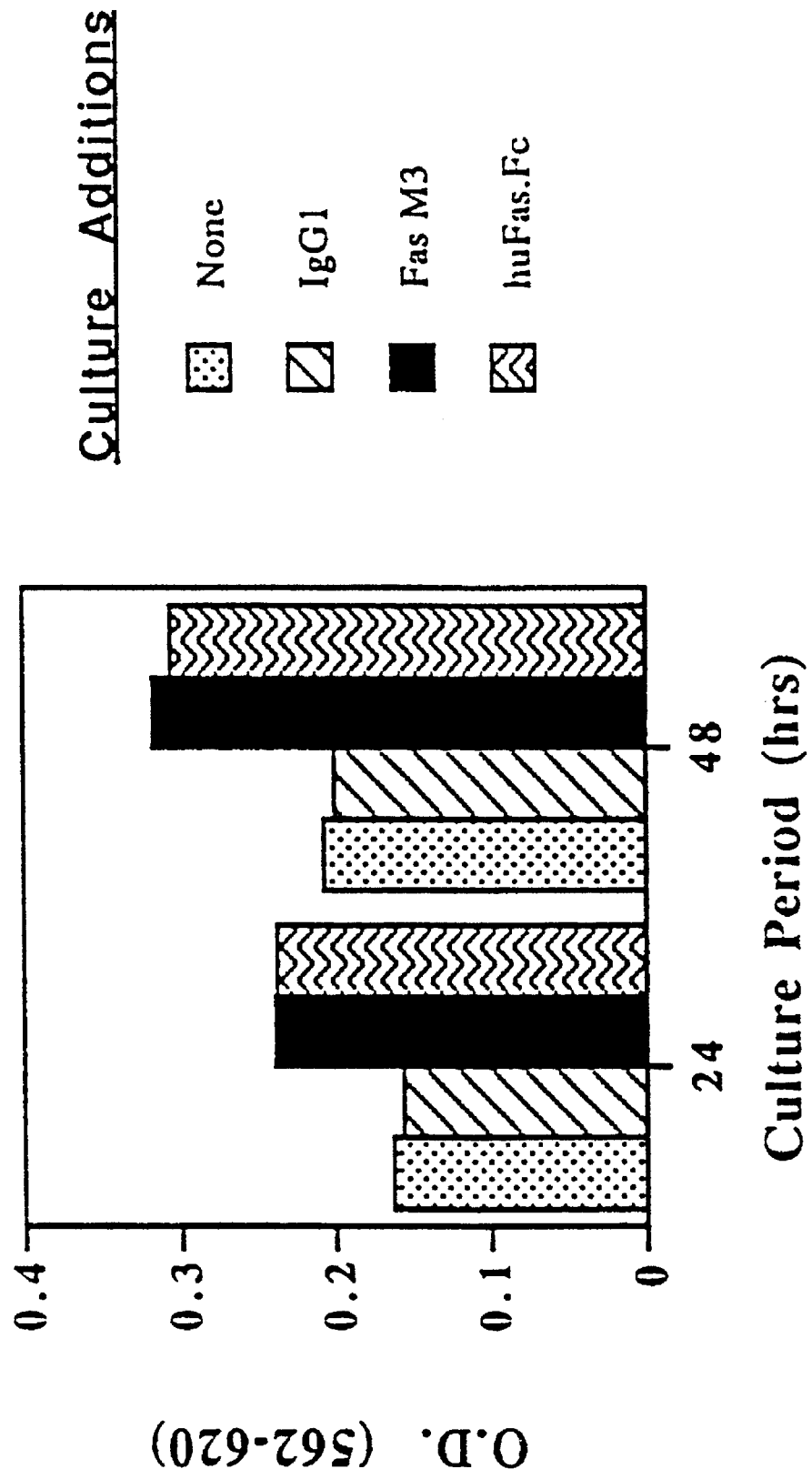

Finally, to determine whether blocking of TCC suicide was due to interference with the interaction of Fas with its ligand or whether the Fas M3 monoclonal antibody acted by signaling the T cell directly, the huFas/Fc fusion protein was used. The huFas/Fc fusion protein blocked activation-induced apoptosis similar to huFas M3 monoclonal antibody, whereas as a control IgG1 immunoglobulin had no effect (FIG. 7C). Thus, the data are consistent with the interpretation that activation induced apoptosis in TCC is mediated, at least in part, by the interaction of Fas with its ligand.

The present invention provides the monoclonal antibodies described above and listed in Table 1, as well as antigen-binding fragments of these antibodies. As illustrated in example 10, F(ab)'$_2$ fragments of monoclonal antibodies M3 and M38 exhibited the same properties as the corresponding whole antibodies in an assay for inhibition of Fas-L mediated lysis of cells bearing Fas antigen. Antibody fragments may be produced by known methods that involve enzymatic treatment of the whole antibody, or by using recombinant DNA technology.

The IgG1 isotype Fas monoclonal antibodies, binding proteins, and purified huFas/Fc fusion protein of the present invention have many uses. For example, IgG1 isotype Fas monoclonal antibodies may be used to detect the presence of Fas in cell cultures and in affinity chromatography to purify Fas antigen. The antibodies also may be utilized in flow cytometry to sort Fas antigen bearing cells or to histochemically stain Fas antigen bearing cells. Briefly, in order to detect Fas antigen on cells, the cells are use within the present invention are well known in the art including, among others, fluorescein isothiocyanate (FITC), phycoerythrin (PE), horse radish peroxidase (HRP), radionuclides and colloidal gold. Also, biotin followed by a streptavidin second step that is conjugated to FITC or more preferably PE or HRP may be used. Particularly preferred for use in flow cytometry is FITC which may be conjugated to purified antibody according to the method of Keltkamp, *Immunology,* 18: 865–873 (1970). See also Keltkamp, *Immunol.,* 18: 875–881 (1970); and Goding, *J. Immunol. Methods,* 13: 215–226 (1970). For histochemical staining, HRP is preferred and may be conjugated to the purified antibody according to the method of Nakane and Kawaoi, *J. Histochem. Cytochem.,* 22: 1084–1091 (1974). See also Tijssen and Kurstak, *Anal. Blochem.,* 136: 451–457 (1984). The antibodies find further use as carriers for delivering cytotoxic agents attached thereto to $Fas^+$ cells. Conjugates comprising a monoclonal antibody listed in Table 1 and a diagnostic or therapeutic agent attached to said antibody are provided herein.

IgG1 isotype Fas monoclonal antibodies and binding proteins may be used as research tools to study the effects of inhibiting the biological activity of Fas and to elucidate the etiology of disorders of the immune system. Such disorders include, but are not limited to, systemic lupus erythematosus (SLE), rheumatoid arthritis, other diseases characterized by arthritic conditions (e.g., lyme disease), idiopathic $CD4^+$T lymphocytopenia, and human immunodeficiency vines (HIV) infection. As discussed above, mice homozygous for the lpr mutation have defects in the Fas antigen gene and do not express normal functional Fas protein capable of transducing the apoptotic signal (Watanabe-Fukunaga et al., *Nature* 356: 314–17, 1992). These mice develop disorders characterized by the accumulation of $CD4^-$ $CD8^-$ T cells in lymph nodes and the spleen, hypergammaglobulinemia, autoantibody production, rheumatoid factor, arthritis, and glomerulonephritis. Id. The antibodies of the present invention find use in studies of the disorders associated with the lpr mutation.

Purified IgG1 isotype Fas monoclonal antibodies and binding proteins may also be utilized therapeutically to block the binding of Fas-L to Fas antigen in vivo, or for in vivo neutralization or costimulation of Fas antigen beating cells. Within preferred embodiments, the antibody is modified to escape immunological detection, for example, by transferring the antigen-binding site of a specific murine monoclonal antibody to a human monoclonal antibody, as discussed above. Particularly preferred is the use of therapeutic compositions comprising an antibody or binding protein to the human Fas antigen, and a physiologically acceptable carrier or diluent. Suitable carriers or diluents include, among others, neutral buffered saline or saline mixed with nonspecific albumin. Additionally, the therapeutic composition may include further excipients or stabilizers antigen, and a physiologically acceptable carrier or diluent. Suitable carriers or diluents include, among others, neutral buffered saline or saline mixed with nonspecific albumin. Additionally, the therapeutic composition may include further excipients or stabilizers such as buffers, carbohydrates including, for example, glucose, sucrose, or dextrose, chelating agents such as EDTA, or various preservatives. Appropriate dosages may be determined in clinical trials, although the amount and frequency of administration may be dependent on such factors as the nature and severity of the indication being treated, the desired response, and the condition of the patient.

Antibodies may also be utilized to monitor the presence of circulating soluble Fas antigen which has been administered to a patient, or to measure in vivo levels of Fas antigen in patients. Within a preferred embodiment, a double determinant or sandwich assay is utilized to detect the Fas antigen. Briefly, serum suspected of containing soluble Fas antigen is incubated with a solid support having a monoclonal antibody, as described above, affixed thereto under conditions and for a time sufficient for binding to occur. Many solid supports are known in the art, including, among others, ELISA plates (Linbro, McLean, Va.), nitrocellulose (Millipore Corp. Bedford, Mass.), beads (Polysciences, Warrington, Pa.), and magnetic beads (Robbin Scientific, Mountain View, Calif.). Additionally, the monoclonal antibody may be readily affixed to the solid support utilizing techniques well known in the art (see *Antibodies. A Laboratory, Manual,* Harlow and Lane (eds.), Cold Spring Harbor Laboratory Press (1988)). The solid support is then incubated with a second labeled monoclonal antibody specific for human Fas antibody under conditions and for a time sufficient for binding to occur, after which presence of bound labeled antibody may be detected.

Within a particularly preferred embodiment, a monoclonal antibody is coated onto a solid support such as a 96 well plate. Subsequently, the plate is blocked with a protein such as bovine serum albumin or nonfat dry milk for about 30 minutes. Serum from a patient is diluted in phosphate buffered saline and incubated in the wells under conditions and for a time sufficient for binding to occur—generally about 30 minutes. Subsequently, the plate is washed and a labeled second monoclonal antibody specific for a different Fas antigen epitope is added into the wells and incubated as described above. Antibodies for different Fas antigen epitopes may be determined through the use of cross-blocking assays. The well is then examined for the presence of the second labeled antibody. Presence of the second labeled antibody indicates the presence of the Fas antigen in the patient's serum. As will be understood by one of ordinary skill in the art, the monoclonal antibodies used within the above assay may be substituted with polyclonal antibodies or binding proteins which are specific for the human Fas antigen.

Certain monoclonal antibodies of the present invention find use when inhibition of Fas-L-mediated apoptosis of Fas antigen-bearing cells is desired. The mAbs may block binding of endogenous Fas-L to the Fas antigen on the cells. Of the mAbs that display antagonistic properties to Fas-L-mediated killing, the M3 and M38 mAbs appear to be the most potent, and are thus preferred for this use. As shown in Table 1, M3 and M38 exhibited the highest level of blocking of Fas-L-mediated lysis of Fas$^+$ cells.

Activated human T cells are induced to undergo programmed cell death (apoptosis) upon triggering through the CD3/T cell receptor complex, a process termed activated-induced cell death (AICD). AICD has been observed in T cells freshly isolated from HIV-infected, but not from uninfected, individuals (Groux et al., *J Exp. Med.,* 175: 331, 1992; Meyaard et al., *Science,* 257: 217, 1992). Thus, apoptosis may play a role in the depletion of CD4$^+$ T cells and the progression to AIDS in HIV infected individuals.

For Fas-L to play a role in T cell depletion in HIV infection, two criteria must be fulfilled. First, Fas-L must be expressed, and therefore T cells must be activated by exposure to antigen. Second, T cells must be "primed" to become susceptible to Fas mediated apoptosis. In HIV$^+$ patients, such priming of T cells may come from cross-linking of CD4 by GP-120/anti-GP-120 complexes. Such complexes have been shown to prime normal CD4$^+$ T cells to undergo AICD in vitro and to cause T cells to undergo apoptosis in mice that express a human CD4 transgene (Wang et al., *Eur. J. Immunol.,* 24: 1553, 1994). In addition, CD4$^+$ T cells undergo apoptotic cell death in mice treated with antibody to CD4, but this phenomenon does not occur in Fas deficient LPR mice (Wang et al., *Eur. J. Immunol.,* 24: 1549, 1994). The AICD seen in activated normal human T cells (such as PL-1 cells) and in freshly isolated T cells from HIV$^+$ individuals is qualitatively identical. Therapeutic intervention for HIV-infected individuals with a Fas antagonist, such as soluble (i.e., non-immobilized) Fas M3 or soluble Fas M38, thus may be possible.

Another use for antagonistic Fas antibodies (such as soluble Fas M3 and soluble Fas M38) is in the ex vivo expansion of T cells for adoptive immunotherapy. One of the limiting steps in expansion of tumor infiltrating lymphocytes (TIL) and cytolytic T cells (CTL) is that these cells can only be expanded for a finite period of time in vitro, which is probably due to AICD. Thus, an antagonistic Fas antibody could be used to expand these T cells for a longer time period in vitro to obtain larger numbers of cells for adoptive transfer.

The T-cells are contacted with the Fas monoclonal antibody during the ex vivo expansion stage. The T-cells may be contacted with the antibody alone, or with the antibody in conjunction with suitable cytokines or other factors that promote proliferation of the T-cells or other desired biological effects. In one embodiment of the invention, the T-cells are cultured in the presence of the Fas antibody and IL-2 during the ex vivo expansion step. Adoptive immunotherapy procedures have been described. See, for example, Rosenberg, S. A., "Adoptive Immunotherapy for Cancer", *Scientific American,* pp. 62–69, May, 1990; and U.S. Pat. No. 5,229,115, hereby incorporated by reference.

For therapeutic use, purified huFas/Fc fusion protein or IgG1 isotype Fas monoclonal antibodies of the present invention are administered to a patient, preferably a human, for treatment in a manner appropriate to the indication. Thus, for example, the pharmaceutical compositions can be administered intravenously, by bolus injection, continuous infusion, sustained release from implants, or other suitable technique. Diseases for which therapeutic treatment with Fas specific mAbs of the present invention may be beneficial include, but are not limited to, SLE, rhematoid arthritis, lyme disease, idiopathic CD4$^+$ T lymphocytopenia, and the effects of human immunodeficiency virus (HIV) infection. One embodiment of the invention is directed to a method of treating such diseases, comprising administering a composition comprising a therapeutically effective amount of monoclonal antibody M3 or M38 and a suitable diluent or carrier to a patient afflicted with such a disease. Such a composition finds use in other disorders in which suppression of Fas-L-mediated apoptosis is desired.

Compositions comprising a Fas/Fc fusion protein and a suitable diluent or carrier are also provided herein. Such compositions find use in inhibiting Fas-L-mediated lysis of cells expressing Fas antigen. The Fas/Fc fusion protein employed in the pharmaceutical compositions should be purified, in that the Fas/Fc fusion protein is substantially free of other proteins of natural or endogenous origin and contains less than about 1% by mass of protein contaminants residual of production processes. Such compositions, however, can contain other proteins added as stabilizers, carriers, excipients or co-therapeutics. The Fas/Fc fusion protein preferably is purified to substantial homogeneity, i.e., is detectable as a single protein band in a polyacrylamide gel by silver staining.

The following examples are provided to illustrate particular embodiments and not to limit the scope of the invention.

EXAMPLE 1

Preparation of soluble huFas/Fc fusion protein

A soluble huFas/Fc protein was constructed in the pDC406 mammalian expression vector by ligating the extracellular domain of the huFas protein to the Fc region of human IgG1. Plasmid pDC406 (C. J. McMahan et al., *EMBO J.*, 10(10): 2821–32 (1991)) is an expression vector that replicates in both mammalian cells and *E. coli* cells.

On the basis of the huFas sequences published by Itoh et al. supra, a cDNA fragment encoding the extracellular region of huFas was obtained using polymerase chain reaction (PCR) techniques. The desired DNA fragment amplified by PCR reaction includes a Asp718 site upstream of a sequence encoding the entire signal sequence and extracellular domain of huFas and a BglII site. The cDNA used as a template in the PCR reaction was cDNA synthesized on RNA isolated from a human T-cell hybridoma designated II-23 (C. F. Ware et al., *Lymphokine Res.*, 5: 313–24 (1986)).

The 5' primer used in the PCR reaction (SEQ ID NO 1) was a single-stranded oligonucleotide of the sequence:

5' CTC GGT ACC AAC AAC CATGCT GGG CAT CTG G 3'

This 5' primer consists of a recognition site for the restriction endonuclease Asp718 (underlined) upstream of a sequence consisting of 23 nucleotides of the huFas nucleotide sequence shown in Itoh et al. beginning eight nucleotides upstream of the translation initiation codon ATG (double underline).

The 3' primer used in the PCR reaction (SEQ ID NO 2) was a single-stranded oligonucleotide of the sequence:

3'CTC CTT CCT AGG TCT AGA TTG AAC 5'

This 3' primer is a sequence of 24 nucleotides that is complementary to the sequence shown in Itoh et al. that encodes the last seven amino acids of the huFas extracellular domain and the first amino acid of the huFas transmembrane domain. The 3' primer includes a recognition site for the restriction endonuclease BglII (underlined) for use in attaching a DNA sequence encoding the Fc-encoding gene.

Those skilled in the art will recognize that many PCR reaction procedures, including those described in Sarki et al., *Science* 239: 487–491 (1988); Wu et al., eds., in *Recombinant DNA Methodology*, pp. 189–196, Academic Press Inc., San Diego (1989); and Innis et al. (eds.), in *PCR Protocols: A Guide to Method and Applications*, Academic Press, Inc. (1990), are suitable procedures; however, the following PCR procedure is provided merely as an example. 10 µl of 10X PCR buffer (500 mM KCl, 100 mM Tris-HCl, pH 8.3 at 25° C., 25 mM MgCl$_2$, and 1 mg/ml gelatin) (Perkins-Elmer Cetus, Norwalk, Conn.), 8 µl of a 2.5 mM solution containing each dNTP (2 mM dATP, 2 mM dCTP, 2 mM dGTP and 2 mM dTFP), 2.5 units (0.5 µl of standard 5000 units/ml solution) of Taq DNA polymerase (Perkins-Elmer Cetus), 1 ng of template DNA, 100 picomoles of each of the oligonucleotide primers, and water to a final volume of 100 µl are added to a 0.5 ml Eppendorf microfuge robe as PCR reagents. The final mixture is then overlaid with 100 µl paraffin oil. PCR is carried out using a DNA thermal cycler (Ericomp, San Diego, Calif.).

In a preferred procedure, the template was denatured at 94° C. for 4 minutes, followed by 5 cycles of 94° C. for 1 minute (denaturation), 55° C. for 1 minute (annealing), and 72° for 2 minutes (extension); followed by 30 cycles of 94° C. for 1 minute, 65° C. for 1 minute, and 72° for 2 minutes; and the last cycle was followed by a final extension at 2° C. for 5 minutes. The PCR reaction products were digested with Asp718 and BglII, and the desired fragment was purified by gel electrophoresis.

A DNA sequence encoding a human IgG1 antibody Fc fragment was prepared as follows and fused to the huFas-encoding DNA fragment to form the soluble huFas/Fc fusion protein. DNA encoding a single chain polypeptide derived from the Fc region of a human IgG1 antibody was cloned into the SpeI site of the pBLUESCRIPT SK® vector (Stratagene Cloning Systems, La Jolla, Calif.). This plasmid vector is replicable in *E. coli* and contains a polylinker segment with 21 unique restriction sites. The DNA sequence of the cloned Fc cDNA coding sequence is presented in SEQ ID NO 3. A unique BglII site was introduced at the 5' end of the inserted Fc encoding sequence, nucleotides 1 through 6 (AGA TCT) in SEQ ID NO 3.

The Fc polypeptide encoded by the DNA extends from the N-terminal hinge region to the native C-terminus, i.e., is an essentially full-length antibody Fc region. The recombinant vector containing the Fc sequence is digested with BglII (which cleaves only at the unique BglII site at nucleic acids 1 through 6 in SEQ ID NO 3) and NotI (which cleaves the vector in the multiple cloning site downstream of the Fc cDNA insert). The Fc-encoding fragment (about 700 bp in length) was isolated by conventional procedures using LMT agarose gel electrophoresis.

The Asp718/BglII huFas-encoding DNA fragment and the BglII/NotI Fc-encoding DNA fragment prepared above initially were ligated into a pDC302 expression vector. A three-way ligation to join the vector, Fc, and huFas DNA fragments was conducted under conventional conditions and *E. coli* cells were transformed with the ligation mixture. A recombinant plasmid containing the insert in the desired orientation (i.e., the huFas sequence was fused in the same reading frame to the downstream Fc sequence as shown in SEQ ID NO 4) was isolated. The SEQ ID NO 4 includes the eight nucleotides immediately upstream of the translation initiation codon ATG of huFas and all but the last three of the nucleotides encoding the extracellular domain of huFas. SEQ ID NO 4 also includes all but the first six nucleotides of SEQ ID NO 3.

Later the Asp718/NotI DNA insert was isolated from the pDC302/huFas/Fc construct, its ends were blunted with klenow, and the DNA insert was cloned into pDC406 to enable large scale transfection in CV-1/EBNA cells. Fas/Fc fusion molecules preferably are synthesized in recombinant mammalian cell culture because they are generally too large and complex to be synthesized by prokaryotic expression methods. Examples of suitable mammalian cells for expressing a receptor/Fc fusion protein include CV-1 cells (ATCC CCL 70) and COS-7 cells (ATCC CRL 1651). Both CV-1 and COS-7 cells are derived from monkey kidney.

The DNA construct pDC406/huFas/Fc was transfected into the monkey kidney cell line CV-1/EBNA (ATCC CRL 10478). The CV-1/EBNA cell line was derived by transfection of the CV-1 cell line (ATCC CCL 70) with a gene encoding Epstein-Barr virus nuclear antigen-1 (EBNA-1) that constitutively expresses EBNA-1 driven from the human CMV intermediate-early enhancer/promoter as described by C. J. McMahan et al., *EMBO J.*, 10(10): 2821–32 (1991). The EBNA-1 gene allows for episomal replication of expression vectors, such as pDC406, that contain the EBV origin of replication. In mammalian host cells such as CV-1/EBNA, the huFas/Fc fusion protein is expressed off the HIV transactivating region (TAR) promoter.

CV-1/EBNA cells transfected with the pDC406/huFas/Fc vector were cultivated in roller bottles to allow transient expression of the fusion protein, which is secreted into the culture medium via the Fas signal peptide. The huFas/Fc fusion protein was purified by affinity chromatography: one liter of culture supernatant containing the huFas/Fc fusion protein was purified by filtering the supernatants (e.g., in a 0.45μ filter) and applying the filtrate to a protein G affinity column (Schleicher and Schuell, Keene, N.H.) according to manufacturer's instructions. The Fc portion of the fusion protein was bound by the protein G on the column. Bound fusion protein was eluted from the column and the purity confirmed on a silver stained SDS gel.

EXAMPLE 2

Generation of huFas monoclonal antibodies

BALB/cJ mice (The Jackson Laboratory, Bar Harbor, Me.) were immunized with huFas/Fc in Freund's adjuvant. Mice were boosted 6 times and spleen cells were fused with the murine myeloma 8.653 in the presence of 50% PEG/10% DMSO in PBS followed by culture in DMEM/HAT and DMEM/HT selective media. Supernalants from positive wells were tested for the ability to bind biotinylated huFas/Fc in an ELISA and by reactivity to huFas/Fc in Western and dot blots. Hybridomas that produced monoclonal antibodies positive for binding to huFas/Fc but not to human IgG1 were cloned by limit dilution 3 times. All monoclonal antibodies (Table 1) were determined to be of the IgG1 isotype and were purified by protein A affinity chromatography.

The monoclonal antibodies were also tested for reactivity with cell surface Fas expressed by both T-lymphoma Jurkat cells (American Type Culture Collection, Rockville, Md. (hereinafter "ATCC")) and the EBV B-cell line, MP-1, by flow cytometry. MP-1 is a spontaneous EBV-transformed B-cell line generated in our laboratory. Cell lines were maintained by continuous passage in RPMI culture medium supplemented with 10% FCS, $5 \times 10^{-5}$M 2-ME, 1 mM sodium pyruvate, 0.1 mM nonessential amino acids, 50 U/ml penicillin and 50 μg/ml streptomycin.

Cells analyzed for Fas expression were first incubated at 4° C. in a blocking solution of PBS containing 2% normal rabbit serum and 2% normal goat serum to prevent non-specific binding of mouse Ig. Cells were washed in FACS buffer (PBS/1% FCS/0.02% sodium azide) and incubated with the appropriate monoclonal antibodies (5 μg/ml) for 30 minutes at 4° C. in a total volume of 50 μl. Cells were then washed and incubated in 50 μl of a 1:40 dilution of goat anti-mouse IgG-PE (Tago, Burlingame, Calif.) for 30 minutes at 4° C. For two-color staining of cultured T cells, CD4-PE or CD8-PE were used in conjunction with CD25-FITC or CD69-FITC monoclonal antibodies. Quadrants were set by analysis of cells incubated with PE-and FITC-conjugated isotype matched control antibodies. Flow cytometry was performed using a FACScan (Becton-Dickinson) and data were collected on $10^4$ viable cells.

EXAMPLE 3

Inhibition of CH-11 binding

The ability of the Fas monoclonal antibodies listed in Table 1 to block the binding of the CH-11 Fas monoclonal antibody to Jurkat cells or MP-1 cells was assessed by flow cytometry. Jurkat cells or MP-1 cells were blocked as above in Example 2 and incubated with a test IgG1 Fas monoclonal antibody at 50 μg/ml for 30 minutes at 4° C. The CH-11 monoclonal antibody (Medical and Biological Laboratories, Magoya, Japan) was then added at 5 μg/ml and incubated for 30 minutes at 4° C. The cells were washed twice with FAGS buffer and incubated with an anti-mouse IgM-FITC (Tago) which has no cross-reactivity with mouse IgG1. Flow cytometry was performed using a FAGS-can (Becton-Dickinson) and data were collected.

The IgG1 Fas monoclonal antibodies varied in their ability to block CH-11 binding from less than 5% inhibition for huFas M31 and M38 monoclonal antibodies up to 62.4% inhibition with huFas M35 monoclonal antibody (Table 1).

EXAMPLE 4

Lysis of Fas expressing cells

An overnight $^{51}$Cr-release assay was used to measure cell lysis induced by huFas monoclonal antibodies. For the overnight $^{51}$Cr-release assay, Jurkat or MP-1 cells were labeled with 150 μCi of $^{51}$Cr for 1 hour at 37° C. For testing monoclonal antibodies in solution, serial dilutions were made in 100 μl of culture medium in 96-well round-bottomed plates (Corning Glass Works, Corning N.Y.). For solid-phase binding of antibodies, dilutions were made in PBS and allowed to incubate on culture plate wells for 4 hours at room temperature followed by 4 washes with PBS and addition of 100 μl of culture medium after the final wash. Ten thousand $^{51}$Cr-labeled targets were then added in 100 μl of medium. After overnight culture at 37° C., plates were centrifuged (150 g for 5 minutes) and supernatants harvested using a Skatron SCS harvesting system (Skatron, Sterling Va.). $^{51}$Cr content of supernalants was determined using a Micromedic ME Plus gamma counter (Micromedics, Huntsville, Tenn.). The percentage of specific $^{51}$Cr-release was calculated according to the formula:

$$1.00 \times [(\text{experimental cpm}) - (\text{spontaneous cpm})] / [(\text{maximum cpm}) - (\text{spontaneous cpm})],$$

where spontaneous cpm=cpm released in medium alone and maximum cpm=cpm released in the presence of 1N HCl.

The cytolytic data summmarized in Table 1 were generated using the above overnight $^{51}$Cr-release assay. Some of the IgG1 isotype Fas monoclonal antibodies (M23, M31, M33, and M35) have no cytolytic potential either in solution or when immobilized. The only monoclonal antibody to cause detectable lysis of Jurkat and MP-1 cells when added to cultures in solution was huFas M2. As indicated in Table 1, M2 in solution caused greater than 10% but less than 30% lysis, and the other antibodies tested caused less than 10% lysis of the Fas-expressing cells. However, although huFas M2 in solution induced target cell lysis at concentrations as low as 100 ng/ml, maximal $^{51}$Cr-release was only 17% at 1 μg/ml as compared to 78% with CH-11 (also at 1 μg/ml) in the same experiment.

The other IgG1 isotype Fas monoclonal antibodies (M1, M3, M24, and M38) were not cytolytic in solution but were at least slightly cytolytic when immobilized. Of these, M1 and M3 were strongly lytic when immobilized on the culture plate. For example, the activity of solid-phase huFas M3 was similar to, or greater than, that of soluble CH-11 when the antibodies were used at their optimal concentration. As shown in Table 1, monoclonal antibodies of the present invention, when immobilized, were characterized as causing less than 10% lysis, less than 30% lysis, less than 50% lysis, or greater than 50% lysis of Fas-expressing cells.

EXAMPLE 5

Inhibition of CH-11-mediated lysis

The ability of the soluble IgG1 huFas-specific monoclonal antibodies to inhibit lysis of either Jurkat or MP-1 cells induced by the CH-11 monoclonal antibody was assessed. The blocking assay used involved making serial dilutions of IgG1 Fas antibodies, adding $^{51}$Cr-labelled Jurkat or MP-1 cells and a constant concentration of CH-11 known to lyse the Jurkat cells and MP-1 cells (e.g., 100 ng/ml), incubating overnight, and assaying for $^{51}$Cr-release from lysed cells using the overnight $^{51}$Cr-release assay described in Example 4 above. The results are presented in Table 1.

As indicated in Table 1, the present invention provides monoclonal antibodies that at about a 10:1 molar ratio inhibit anti-Fas CH-11 monoclonal antibody-mediated lysis of cells by greater than 10%. Certain monoclonal antibodies of the present invention inhibited said lysis by greater than 50%, and still others inhibited said lysis by at least 90%. Consistent with their ability to cause 5partial blocking of CH-11 binding to Fas expressing cells, several monoclonal antibodies inhibited CH-11-mediated cell lysis (Table 1). On the other hand, huFas M38 monoclonal antibody failed to block binding of CH-11 but it efficiently inhibited CH-11-induced target cell lysis. The M23, M31, and M33 monoclonal antibodies were found to bind to cell surface Fas yet neither induced nor inhibited apoptosis.

Monoclonal antibody huFas M3 was strongly lytic when immobilized, failed to lyse cells when added in solution, and inhibited cell lysis induced by the CH-11 monoclonal antibody. This shows that huFas M3 can act as a CH-11 agonist when bound to plastic but as an antagonist when added in a soluble form. The cell lysis induced by immobilized huFas M3 is characteristic of apoptosis in that DNA laddering similar to that induced by soluble CH-11 was observed in both MP-1 and Jurkat cells. Furthermore, DNA laddering induced by the CH-11 monoclonal antibody was completely abrogated by addition of soluble huFas M3. On the other hand, huFas M38 monoclonal antibody failed to block binding of CH-11 but it efficiently inhibited CH-11-induced target cell lysis. Thus, huFas M38 appears to inhibit CH-11-mediated apoptosis of target cells by binding to an epitope that is not recognized by the CH-11 antibody.

EXAMPLE 6

Costimulation of T lymphocyte activation

Flow cytometry was used to assess the ability of our huFas-specific monoclonal antibodies to bind to freshly isolated normal human leukocytes or leukocytes cultured with mitogenic stimuli. For the flow cytometry, cells to be analyzed for Fas expression were first incubated at 4° C. in a blocking solution of PBS containing 2% normal rabbit serum and 2% normal goat serum to prevent non-specific binding of mouse Ig. Cells were washed in FACS buffer (PBS/1% FCS/0.02% sodium azide) and incubated with the appropriate monoclonal antibody (5 µg/ml) for 30 minutes at 4° C. in a total volume of 50 µl. Cells were then washed and incubated in 50 µl of a 1:40 dilution of goat anti-mouse IgG-PE (Tago, Burlingame, Calif.) for 30 minutes at 4° C. Specific binding of huFas monoclonal antibodies to neutrophils, monocytes, SAC-activated B cells and PHA-induced T-cell blasts was detected. In addition, none of these cell types was induced to undergo cytolysis when cultured with either soluble or immobilized huFas monoclonal antibodies in the overnight $^{51}$Cr-release assay described in Example 2 above.

A T cell costimulation assay was used to determine whether immobilized IgG1 isotype huFas monoclonal antibodies would costimulate T cells in conjunction with solid-phase CD3 monoclonal antibody. T cells were enriched from PBMC by rosetting with 2-aminoethyl isothiouronium bromide hydrobromide-treated SRBC. Monocytes were depleted by plastic adherence for 1 hour at 37° C. and the resulting population of cells was greater than 95% CD3$^+$ by flow cytometry. Peripheral blood T cells were cultured at 1×10$^5$ per well in 96-well flat-bottomed plates that had been previously coated with monoclonal antibodies as described above. Peripheral blood T cells were cultured with immobilized huFas monoclonal antibodies in the presence or absence of immobilized CD3 monoclonal antibody, incubated at 37° C. in a humidified atmosphere of 5% CO$_2$ in air for 3 days and pulsed with 1 µCi of $^3$H-TdR for the final 6 hours of culture. Wells were then harvested and incorporated radioactivity determined using a Matrix 96 beta counter (Packard, Meriden, Conn.).

The results obtained using the complete panel of huFas monoclonal antibodies are summarized in Table 1. Some, but not all, of the IgG1 isotype huFas monoclonal antibodies were found to be strong costimulators of T-cell proliferation with activity equivalent to, or greater than, that of IL-2. For example, huFas M38 costimulated T cell proliferation at concentrations as low as 100 ng/ml (FIG. 1A). The huFas monoclonal antibodies, including CH-11, costimulated T cells only when immobilized and not when added to cultures in solution. For most of the IgG1 isotype Fas monoclonal antibodies, the ability to induce lysis of Fas-expressing cell lines correlated with their costimulatory activity on T cells. However, huFas M35 and M38 were potent costimulators of T-cell proliferation, but had little or no activity in the cytolysis assays. In contrast, the CH-11 monoclonal antibody lyse Jurkat and MP-1 targets when added in solution and yet can only costimulate T cells with CD3 monoclonal antibody when immobilized on the culture well.

Thymocytes obtained from infants undergoing corrective cardiac surgery and isolated by Ficoll density centrifugation also were assessed to determine whether they could be activated by IgG1 huFas monoclonal antibodies. Thymocytes were cultured at 1×10$^5$ per well in 96-well flat-bottomed plates that had been previously coated with monoclonal antibodies as described above. Thymocytes were cultured with immobilized huFas monoclonal antibodies in the presence or absence of immobilized CD3 monoclonal antibody, incubated at 37° C. in a humidified atmosphere of 5% $CO_2$ in air for 3 days and pulsed with 1 μCi of $^3$H-TdR for the final 6 hours of culture. Wells were then harvested and incorporated radioactivity determined using a Matrix 96 beta counter (Packard, Meriden, Conn.). Human thymocytes were costimulated to proliferate by immobilized huFas M38 monoclonal antibody in the presence of immobilized CD3 monoclonal antibody (FIG. 1B).

To analyze the effect of Fas monoclonal antibodies on human T cells in more detail, flow cytometry and the T cell costimulation assay as described above were used to determine whether the costimulation of peripheral blood T cells by huFas monoclonal antibodies was accompanied by enhanced expression of T-cell activation molecules. Two such molecules, the early activation antigen CD69 and the p55 low affinity chain of the IL-2 receptor CD25, were strongly enhanced on both $CD4^+$ and $CD8^+$ T cells stimulated with huFas M38 plus immobilized CD3 monoclonal antibody compared to immobilized CD3 monoclonal antibody alone (FIGS. 2A–2H). For two-color staining of cultured T cells, CD4-PE or CD8-PE were used in conjunction with CD25-FITC or CD69-FITC monoclonal antibodies. Quadrants were set by analysis of cells incubated with PE-and FITC-conjugated isotype matched control antibodies. Flow cytometry was performed using a FACScan (Becton-Dickinson) and data collected on $10^4$ viable cells. Enhanced expression of CD25 and CD69 was detected on both $CD4^+$ and $CD8^+$ T cells. Ligation of Fas by immobilized huFas M38 in the presence of immobilized CD3 monoclonal antibody also induced modest increases in expression of the adhesion molecules CD11a (LFA-1), CD18 and CD54 (ICAM-1).

EXAMPLE 7

Cytokine assays

To determine whether the activation of human T cells by Fas monoclonal antibodies was dependent upon soluble cytokine production two approaches were used. First, an assessment of whether T cells costimulated with Fas monoclonal antibodies increased their cytokine production was made. Second, T cells were costimulated with Fas monoclonal antibodies in the presence or absence of a neutralizing IL-2 antiserum. For the cytokine assay, cultures for the measurement of IL-2 production were performed in the presence of an IL-2R p55 monoclonal antibody to prevent utilization of IL-2 produced by the T cells. IL-2 levels were measured with a CTLL bioassay (S. Gillis et al. *J. Immunol.*, 120: 2027–32 (1978)) using recombinant human IL-2 as a standard. IFN-γ and TNF-α levels were determined by ELISA, as described by M. R. Alderson et al., *J. Exp. Med.* 173: 923–30 (1991).

Figure 3A:
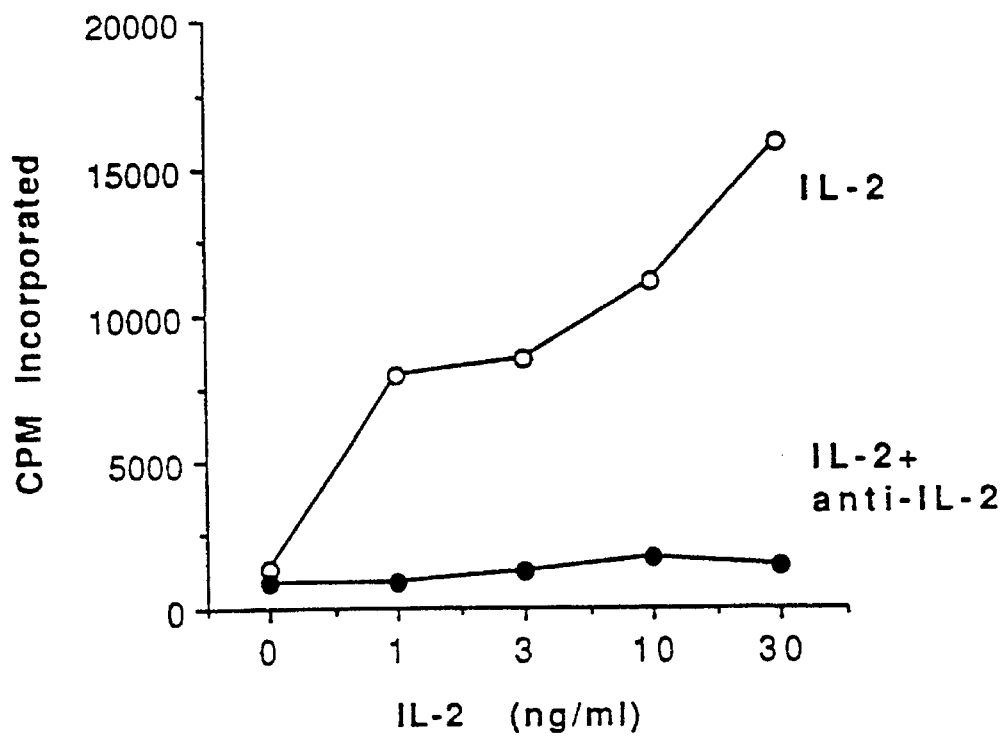
FIGS. 3A and 3B show that costimulation of T cell proliferation by huFas monoclonal antibody M38 is largely 1L-2-independent.
Figure 3B:
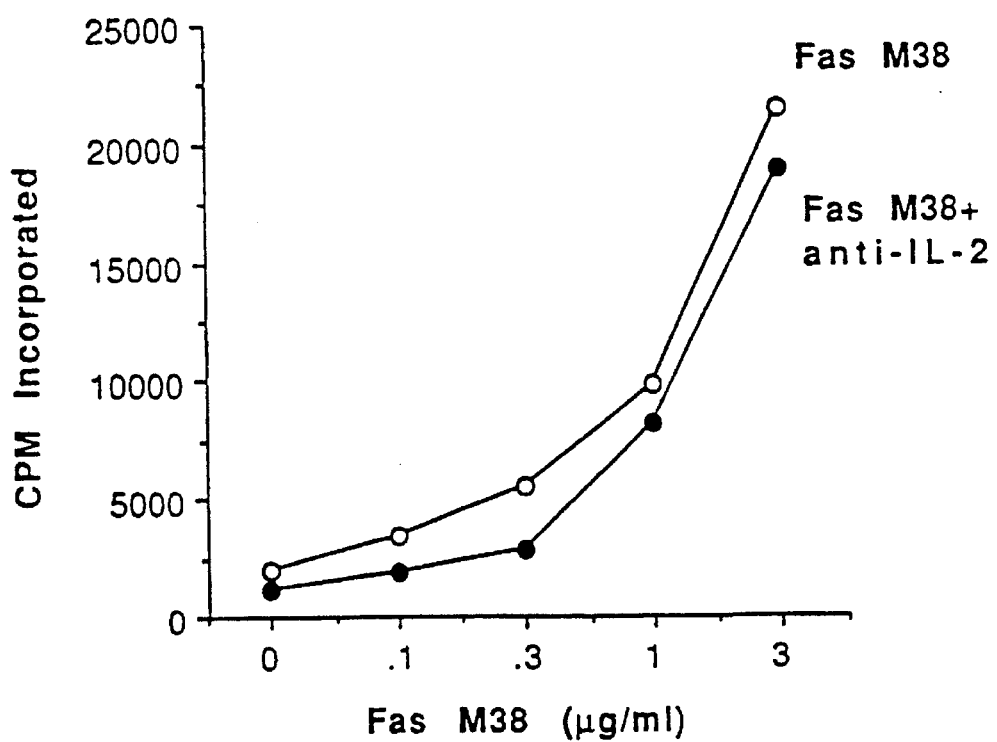

T cells stimulated with huFas M38 plus CD3 monoclonal antibody were found to produce approximately 10-fold more IL-2, IFN-γ, and TNF-α than cells stimulated with CD3 monoclonal antibody alone (Table 2). In a second experiment, cells were costimulated with huFas M38 monoclonal antibody in the presence or absence of a neutralizing Il-2 antiserum. Although this antiserum completely neutralized the effect of exogenous IL-2 on T-cell proliferation over a wide range of IL-2 concentrations (FIG. 3A), it had only a minimal effect on Fas monoclonal antibody costimulation (FIG. 3B).

EXAMPLE 8

Limiting dilution analysis

To address the question of whether the T cells were the direct target of action of Fas monoclonal antibodies in T-cell activation or whether interactions with accessory cells were required, we used limit dilution analysis in Terasaki microcultures and analyzed the frequency of T cells responsive to Fas monoclonal antibodies. For the limit dilution analysis, the frequency of proliferating human T-cell precursors was assessed in microcultures as described for murine T cells by E. Maraskovsky et al., *Int. Immunol.* 3(3): 255–64 (1991); E. Maraskovsky et al., *Int. Immunol.* 4(4): 475–85 (1992). Using this limit dilution analysis, T cells were cultured in 60-well Terasaki trays that had been pre-coated with OKT3 (10 μg/ml) with or without huFas M38 monoclonal antibody (10 μg/ml) overnight at 4° C. Cells were cultured in the presence of IL-2 (10 ng/ml) in a total volume of 15 μl at 1 to 20 cells/well. After 5 days of culture, wells were visually examined for the presence or absence of proliferating T cells using an inverted phase-contrast microscope. A well was scored positive if one or more clusters of at least 3 blast cells were observed or if the number of blasts present was greater than the input number. Estimates of the frequency of proliferating cell precursors were determined from the Poisson distribution relationship between the number of input cells and the percent negative wells using the minimum $\chi^2$ method described by C. Taswell, *J. Immunol.* 126: 1614–19 (1981). Clone size estimates were made by counting the number of cells per well and then adjusting for clonal overlap based upon the Poisson distribution.

The linear relationship between the number of input cells and the log of the percent negative wells (FIG. 4) suggests that the precursor T cell was the limiting component in these cultures. Although the response varied with different T-cell donors, Fas M38 consistently enhanced the frequency of proliferating T-cell clones by at least 3-fold and increased the average clone size by approximately 2-fold (Table 3).

EXAMPLE 9

B10 anti-B10.5 cell line development

To detect the expression of a ligand for Fas, a highly sensitive three-step flow cytofluorometric assay was used. In the assay, cells to be evaluated for expression of Fas-L were first blocked by incubation in FACS buffer containing 1% normal mouse serum, 50 μg/ml purified rat anti-mouse FcRTγII (2.4G2), and 0.01% $NaN_3$ ($5\times10^5$ cells per well in a 96-well microtiter plate) at 4° C. in a total volume of 20 μl. Cells were then sequentially incubated with the indicated fusion protein (huCD69/Fc, huIL4R/Fc, HSA/Fc, huFas/Fc or huTNFR/Fc) followed by biotinylated mouse anti-huIgG$_1$ (Fc-specific; Jackson Laboratories, West Grove, Pa.), and streptavidin-phycoerythrin (Tago, Burlingame, Calif.). After the final wash, cells were resuspended in 0.3 ml FACS buffer containing 10 ng/ml propidium iodide. Flow cytometry was performed using a FACScan (Becton-Dickinson) and data collected on 1×10⁴ viable cells were analyzed using LYSYS II software.

Using this assay, low level binding of huFas/Fc to a long-term CD8⁺ murine anti-tumor T cell line (B10 anti-B10.5) was detected after stimulation of the T cells with PMA and ionomycin for 2 hours. The B10 anti-B10.5 cell line was developed from lymphoid cells of C57Bl/10SnJ (B10) origin responsive to a syngeneic fibrosarcoma (B10.5) (D. H. Lynch and R. E. Miller, *Eur. J. Immunol.*, 21: 1403–10 (1991) and D. H. Lynch et al., *Eur. J. Immunol.*, 21: 2977–85 (1991), as follows: Mice were injected in the hind foot pads with 2–4×10⁶ viable syngeneic tumor cells. Draining lymph nodes (DLN) were aseptically excised 8–12 days later and dissociated into a single cell suspension. Cell cultures were established (in the absence of added tumor stimulator cells) in upright 25 cm² tissue culture flasks at 1.5×10⁶ viable cells/ml (20 ml/flask) in RPMI 1640 medium supplemented with 10% FBS, 2 mM glutamine, 1 mM sodium pyruvate 0.1 mM nonessential amino acids, 5×10⁻⁵M 2-mercaptoethanol, 50 μg/ml streptomycin and 50 U/ml penicillin at 37° C. in a humidified atmosphere of 5% $CO_2$ in air. After four days in culture, the resulting CTL were subcultured in 24-well tissue culture plates at a concentration of 5×10⁵ cells/ml (2 ml/well) in medium supplemented with a mixture of IL-2 and IL-7 (2 ng/ml and 10 ng/ml, respectively) with irradiated (10,000R) tumor stimulator cells. Subcultures were then maintained by weekly feeding with medium containing IL-2 and IL-7 in the absence of additional tumor cell stimulation.

The B10 anti-B10.5 cells were also found to bind TNFR/Fc after stimulation with PMA and ionomycin, but not huIL-4R/Fc, huCD69/Fc or HSA/Fc. These cells also failed to bind CD27/Fc, 4-1BB/Fc, CD40/Fc or muOX40/Fc.

Additional studies have shown that Fas-L can be induced on a variety of different types of both murine and human T cells (Table 4). However, it did not appear to be induced on all of the T cell lines tested. Nor could Fas-L be detected on either murine B cells or human B cell lines. We were unable to detect Fas-L on human peripheral blood neutrophils and the human myelocytic and monocytic cell lines U937 and THP-1.

EXAMPLE 10

Fas-L verification by apoptosis

Both the overnight ⁵¹Cr-release assay (see Example 4) and degradation of target cell DNA into the "ladder" pattern characteristic of the apoptotic process were used to determine whether (1) the cell-surface determinant detected on the B10 anti-B10.5 cells after stimulation with PMA and ionomycin for 2 hours could mediate apoptosis of either Jurkat or MP-1 target cells, and (2) whether the apoptotic process could be inhibited by huFas monoclonal antibodies.

To measure cell lysis induced by cell-surface determinant detected on the activated B10 anti-B10.5 cells, B10 anti-B10.5 cells were activated by incubation for 2 hours in medium containing phorbol ester and calcium ionophore, followed by light fixation (0.6% formaldehyde for 1 minute). Titrated numbers of the fixed, activated B10 anti-B10.5 cells were co-cultured with ⁵¹Cr-labelled Jurkat cells at effector to target cell ratios of 10:1, 3:1, 1:1, and 0.3:1. The cell mixtures were incubated overnight and assayed for ⁵¹Cr-release from lysed cells as described in Example 4 above. Spontaneous ⁵¹Cr-release after overnight culture was 20.3%.

Figure 5:
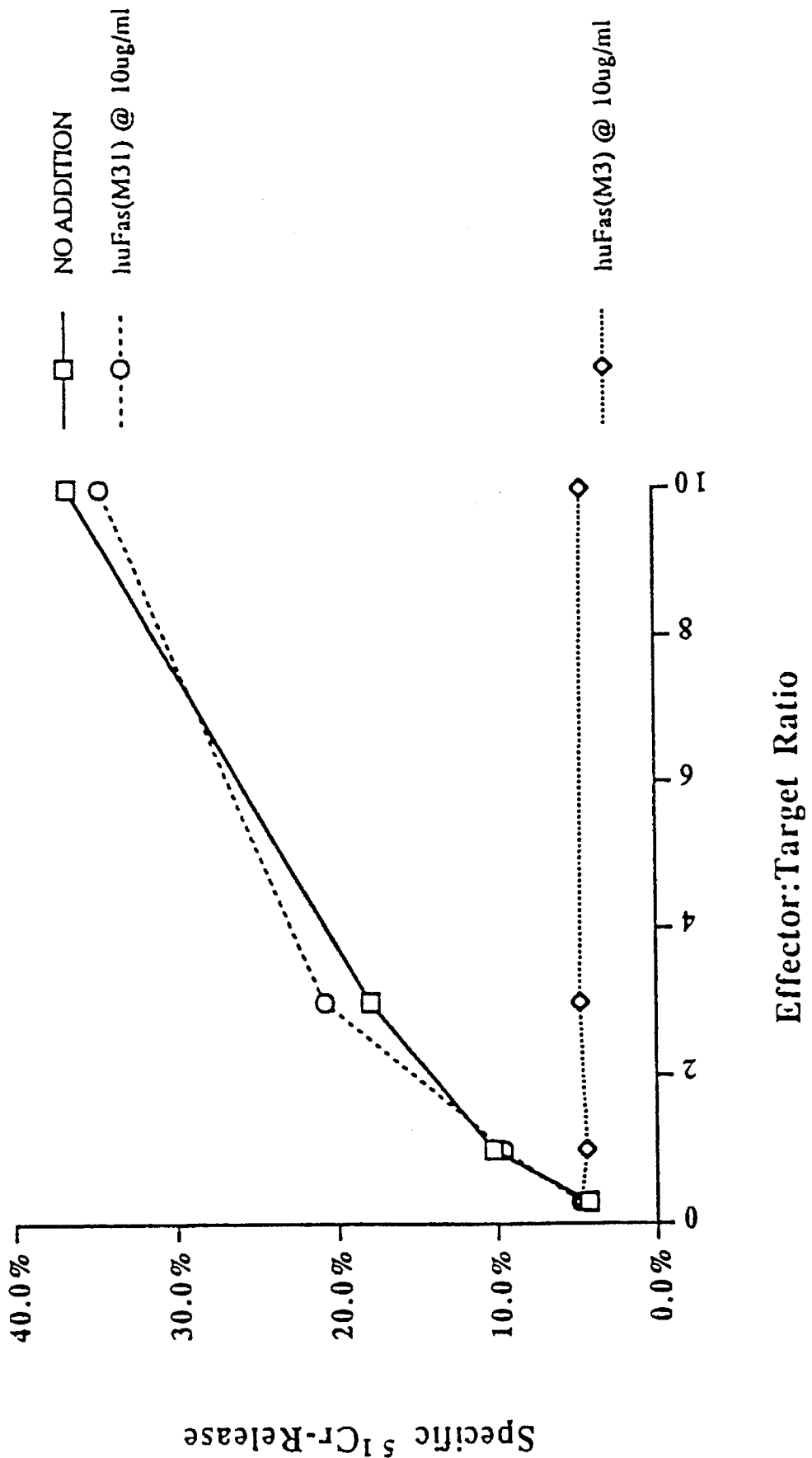
FIG. 5 shows the effect of huFas M3 and huFas M31 on Fas-L-mediated killing of Jurkat cells. Open squares represent controls, open circles represent huFas M31 at 10 μg/ml, and open diamonds represent huFas M3 at 10 μg/ml.

In a blocking assay, B10 anti-B10.5 cells were activated and lightly fixed, as described above. Titrated numbers of the fixed, activated B10 anti-B10.5 cells were co-cultured with ⁵¹Cr-labelled Jurkat cells at effector to target cell ratios of 10:1, 3:1, 1:1, and 0.3:1 in either medium alone or medium containing either huFas M3 or M31 antibodies (10 μg/ml). The cell mixtures were incubated overnight and assayed for ⁵¹Cr-release from lysed cells, as described in Example 4 above. FIG. 5 shows specific released ⁵¹Cr from cell mixtures cultured overnight in medium alone (open square), 10 μg/ml huFas M3 (open diamond) or 10 μg/ml M31 (open circle) monoclonal antibodies. DNA obtained from parallel cultures was evaluated for DNA fragmentation by gel electrophoresis. DNA fragmentation was only observed in those cell mixtures in which significant ⁵¹Cr release was detected. The results for each of the antibodies are summarized in Table 1. The data in Table 1 show that two of the monoclonal antibodies (M3 and M38), at a concentration of 10 μg/ml, were capable of inhibiting greater than 90% of Fas ligand-mediated lysis of Fas-expressing cells. F(ab)'2 fragments of M3 and M38 exhibited the same level of inhibition of Fas ligand-mediated lysis of Jurkat cells as the corresponding whole M3 and M38 antibodies.

Figure 6:
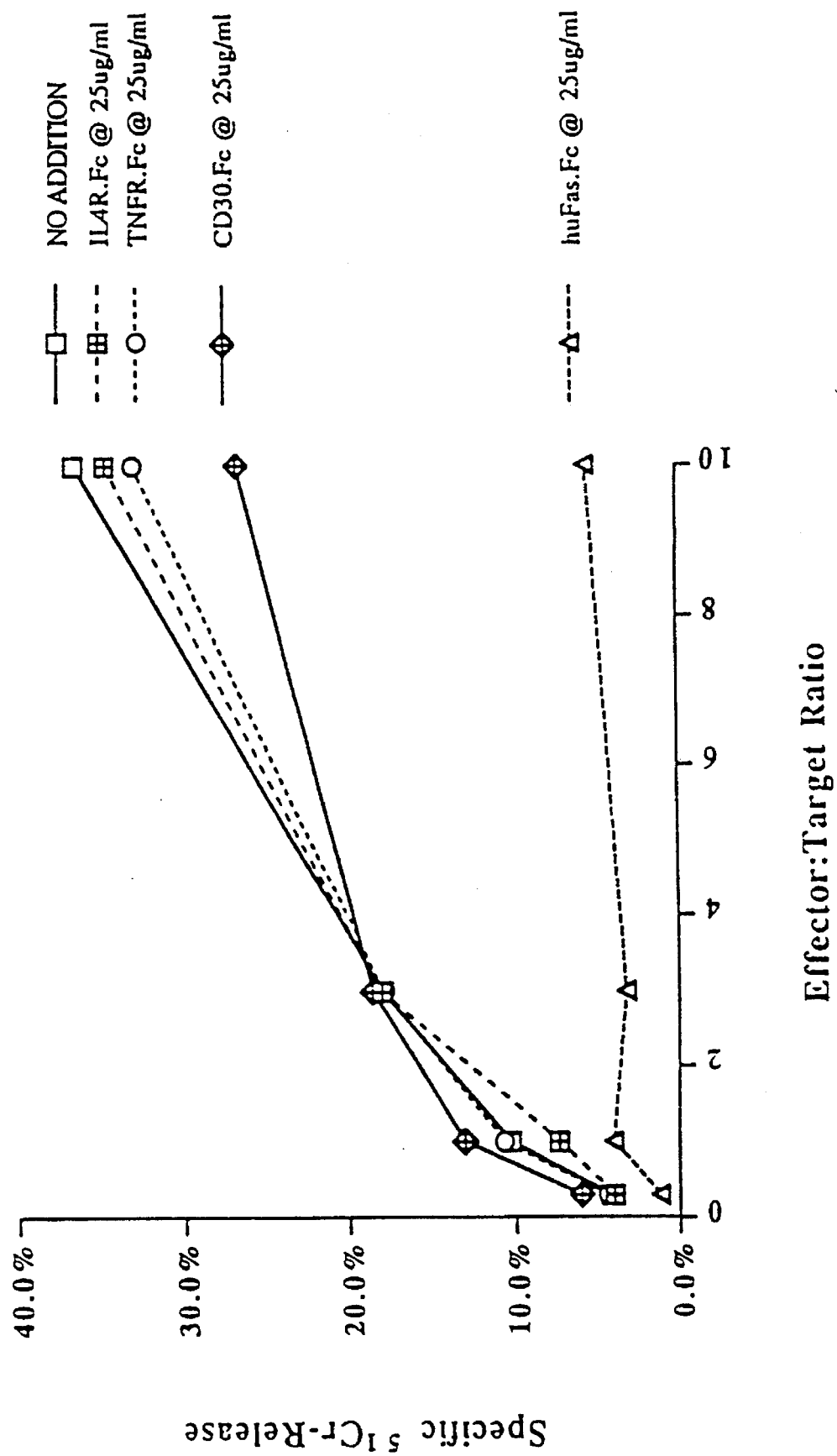
FIG. 6 shows the effect of various soluble fusion proteins on Fas-L-mediated killing of Jurkat cells. huIL4R/Fc (filled square), huCD30/Fc (filled diamond), huTNFR/Fc (open circle), or huFas/Fc (open triangle) were soluble fusion proteins analyzed along with a control (open square).

To confirm that the molecule expressed by the B10 anti-B10.5 cells subsequent to activation with PMA and ionomycin is Fas-L, lytic activity of the activated B10 anti-B10.5 cells used in the above blocking assay was also evaluated in the presence of either medium alone or 25 μg/ml huIL4R/Fc, huCD30/Fc, huTNFR/Fc, or huFas/Fc. Lysis of target cells was inhibited by the huFas/Fc fusion protein but not by huIL-4R/Fc, huTNFR/Fc or CD30/Fc (FIG. 6). DNA was obtained from parallel cultures of the above groups (effector:target ratio=2.5:1) after an 8 hour incubation period and evaluated for DNA fragmentation by gel electrophoresis. DNA fragmentation was only observed in those cell mixtures in which significant ⁵¹Cr release was detected.

EXAMPLE 11

Blocking apoptosis in T cell clones

To address whether activation-induced apoptosis and apoptosis induced by cross-linking Fas may be causally related, antagonists of Fas were used in an attempt to block apoptosis induced by stimulation of long-term cultured human CD4⁺ T cell clones (TCC) by phorbol ester (PMA) and calcium ionophore (ionomycin). In an initial experiment two different TCC (PL-1 and PL-2) were cultured in medium alone, medium containing soluble Fas M3 monoclonal antibody (10 μg/ml), medium containing PMA plus ionomycin (5 ng/ml and 500 ng/ml, respectively), or medium containing Fas M3 monoclonal antibody (10 μg/ml) and PMA plus ionomycin (5 ng/ml and 500 ng/ml, respectively). After 48 hours of culture at 37° C. in a humidified atmosphere of 5%

$CO_2$ in air, cell viability was determined by trypan blue dye exclusion. A significant decrease in cell viability was observed in TCC cultured in medium containing PMA plus ionomycin compared to TCC cultured in medium alone or medium containing Fas M3 monoclonal antibody (FIG. 7A). This effect was completely inhibited by addition of Fas M3 monoclonal antibody to TCC cultured in medium containing PMA plus ionomycin.

In a follow-up experiment, the Fas M3 monoclonal antibody was used to inhibit apoptosis induced by engaging the TCR/CD3 complex (OKT3) or by culturing TCC with PHA or PMA plus ionomycin. To do this, a colorimetric assay was employed in which active mitochondria convert the tetrazolium salt [3-(4,5-dimethylthiazol-2-yl)-2,5-diphenyltetrazolium bromide] (known as MTT) to a blue formazan product. Cloned human T cells ($10^4$ cells per well) are added in a final volume of 100 μl to 96 well plates. Cells are stimulated under a variety of conditions as noted above. To some cultures, either a control murine IgG1 antibody or huFas M3 antibody was added (final concentration 10 μg/ml). Following 24 to 48 hours of culture at 37° C. in a humidified atmosphere of 5% $CO_2$ in air, 10 μl of a 5 mg/ml solution of MTT is added to the wells. The plates are further cultured for another 4 hours to allow for the conversion of MTT by viable, metabolically active cells. Following this incubation, 100 μl of 0.05M HCl in isopropanol is added to the wells. The resulting mixture is vigorously pipetted to dissolve any crystals that form as a result of MTT cleavage. The degree of conversion is determined by reading the plates in a microtiter plate reader (as for an ELISA), using a dual wavelength setting (550 nm–650 nm). A higher level of MTT conversion, as indicated by a higher OD (562–620) reading, is indicative of increased cell viability and metabolic activity.

Soluble Fas M3 monoclonal antibody substantially blocked apoptosis in TCC induced by any one of these engaging the TCR/CD3 complex (OKT3) or by culturing long-term cultured human CD4+ T cell clones (TCC) with PHA or PMA plus ionomycin, as indicated by the increased level of MTT conversion (increased OD 562–620) in cultures that contained soluble huFas M3 monoclonal antibody (FIG. 7B).

In another experiment, to determine whether blocking of TCC suicide was due to interference with the interaction of Fas with its ligand or whether the huFas M3 monoclonal antibody acted by signaling the T cell directly, the Fas/Fc fusion protein was compared to huFas M3 monoclonal antibody and a control IgG1 immunoglobulin and media. Cultures were assayed at 24 and 48 hours after initiation. Cloned human T cells ($10^4$ cells per well) were stimulated with PHA in either medium alone or medium containing a control murine IgG1 antibody, the huFas M3 monoclonal antibody, a huIL-4/Fc fusion protein, or the huFas/Fc fusion protein. After 48 hours of culture at 37° C. in a humidified atmosphere of 5% $CO_2$ in air on MTT conversion assay was performed as described above. The data show that the Fas/Fc fusion protein blocked activation-induced apoptosis just as huFas M3 monoclonal antibody did, whereas IgG1 had no effect (FIG. 7C).

TABLE 1

Characterization of huFas monoclonal antibodies

| Antibody Designation[a] | % inhibition of CH-11 binding[b] | Lysis of Fas expressing cells in solution[c] | Lysis of Fas expressing cells immobilized[c] | Blocking of CH-11 mediated lysis[d] | Costimulation of T cells[e] | Blocking of Fas-L mediated lysis[d] |
|---|---|---|---|---|---|---|
| M1 | 24.1 | − | +++ | ++ | ++ | + |
| M2 | 21.8 | + | +++ | ++ | +++ | − |
| M3 | 44.7 | − | +++ | +++ | +++ | +++ |
| M23 | 45.3 | − | − | − | + | − |
| M24 | 45.9 | − | ++ | + | +++ | + |
| M31 | 0.0 | − | − | − | − | − |
| M33 | 41.8 | − | − | − | − | − |
| M35 | 62.4 | − | − | ++ | +++ | ++ |
| M38 | 4.1 | − | + | +++ | +++ | +++ |

[a]M1–M38 are mouse IgG1 mAb.
[b]% inhibition of CH-11 binding was calculated from the MFI of binding CH-11 to Jurkat or to MP-1 cells alone compared to its binding in the presence of 10-fold excess competing antibody.
[c]Lytic activity was assessed on both Jurkat and MP-1 targets. Lysis by soluble CH-11 mAb at 100 ng/ml was used as a positive reference (i.e. +++). Thus, antibodies giving rise to 50% lysis or more at their optimal concentration were scored as +++, greater than 30% but less than 50% lysis as ++, greater than 10% but less than 30% lysis as +, and less than 10% lysis as −.
[d]Blocking activity was assessed on both Jurkat and MP-1 targets. Antibodies that showed greater than 90% blocking at 10:1 molar ratio (i.e. 1 μg/ml) were scored as +++, greater than 50% but less than 90% inhibition as ++, greater than 10% but less than 50% inhibition as + and less than 10% inhibition as −.
[e]Antibodies that costimulated $^3$H-TdR incorporation equivalent to or better than IL-2 at their optimal concentration were scored as +++, greater than 50% but less than 100% of the IL-2 response as ++, greater than 10% but less than 50% of the IL-2 response as +, and less than 10% of the IL-2 response as −.

TABLE 2

Fas mAb costimulates T-cell cytokine release

| mAb Stimulus | IL-2 (units/ml) | IFN-g (pg/ml) | TNF-a (pg/ml) |
|---|---|---|---|
| Nil | <0.1 | <5 | <5 |
| Fas M38 | <0.1 | <5 | <5 |
| CD3 | 0.8 | 96 | 110 |
| CD3 + Fas M38 | 6.7 | 811 | 1,318 |

TABLE 3

Effect of Fas monoclonal antibody on the frequency and clone size of CD3 monoclonal antibody stimulated T cells

| | Exp 1 | | Exp 2 | | Exp 3 | |
|---|---|---|---|---|---|---|
| Stimulus | % prolif. clones | No. blasts/ clones | % prolif. clones | No. blasts/ clones | % prolif. clones | No. blasts/ clones |
| CD3 mAb | 3.08 | 11 | 1.82 | 11 | 1.05 | 10 |
| CD3 mAb + Fas M38 | 12.6 | 23 | 23.0 | 24 | 14.6 | 24 |

Limiting dilution microcultures were established with approximately 10 T cells/well with 10 ng/ml IL-2 and frequency estimates derived from the Poisson distribution assuming single hit kinetics. Clone size estimates were made by counting the number of blasts per positive well and adjusting for clonal overlap.

TABLE 4

Cells Tested for Expression of Fas Ligand

| Cell | Description |
|---|---|
| *Cell Testing Positive* | |
| aB10.5 | murine CTL (CD8$^+$) |
| 7B9 | murine T$_h$2 |
| lymph node T cells | murine |
| thymocytes | murine |
| thymocytes | human |
| peripheral blood T cells | human |
| PL-1 | human CD4$^+$ T cell |
| PL-2 | human CD4$^+$ T cell |
| clone 14 | human CD4$^+$ T cell |
| B5 | human CD8$^+$ T cell |
| *Cell Testing Negative* | |
| splenic cells | murine |
| MP-1 | human B cell line |
| KC-EBV | human B cell line |
| VB-EBV | human B cell line |
| U937 | human myelocytic cell line |
| THP-1 | human monocytic cell line |
| S49 | murine T cell lymphoma |
| EL4 | murine thymoma |
| SF4 | murine T cell lymphoma |
| aB10.2 | murine CTL (CD8$^+$) |
| neutrophils | human peripheral blood |

What is claimed is:

1. An IgG1 monoclonal antibody that specifically binds to the extracellular domain of human Fas antigen and at a 10-fold molar excess inhibits binding of anti-Fas CH-11 monoclonal antibody to cells expressing Fas antigen within a range from about 4% to about 62%.

2. The monoclonal antibody according to claim 1 wherein said monoclonal antibody is selected from the group consisting of murine and humanized monoclonal antibodies.

3. The monoclonal antibody according to claim 2 that at about a 10:1 molar ratio inhibits anti-Fas CH-11 monoclonal antibody-mediated lysis of cells by greater than 10%.

4. The monoclonal antibody according to claim 3 that at about a 10:1 molar ratio inhibits anti-Fas CH-11 monoclonal antibody-mediated lysis of cells by greater than 90%.

5. The monoclonal antibody according to claim 3 that, when used with an immobilized CD3 monoclonal antibody in a T-cell co-stimulation assay, costimulates the proliferation of T-cells independent of interleukin 2 and in solution causes less than 30% lysis of Fas-expressing cells.

6. The monoclonal antibody according to claim 5 that when crosslinked by immobilization causes less than 50% lysis of Fas-expressing cells.

7. The monoclonal antibody according to claim 6 that when crosslinked by immobilization causes less than 10% lysis of Fas-expressing cells, and that, when used with an immobilized CD3 monoclonal antibody in a T-cell co-stimulation assay, costimulates the proliferation of T-cells equivalent to or better than interleukin 2.

8. The monoclonal antibody according to claim 6 that at about a 10:1 molar ratio inhibits greater than 90% of anti-Fas CH-11 monoclonal antibody-mediated lysis of cells, and that, when used with an immobilized CD3 monoclonal antibody in a T-cell co-stimulation assay, costimulates the proliferation of T-cells equivalent to or better than interleukin 2.

9. An IgG1 monoclonal antibody that:
a) specifically binds to the extracellular domain of human Fas antigen,
b) when used with an immobilized CD3 monoclonal antibody in a T-cell co-stimulation assay, costimulates the proliferation of T-cells independent of interleukin 2, and
c) inhibits Fas ligand-mediated lysis of Fas-expressing cells by at least 10%.

10. The monoclonal antibody according to claim 9 wherein said monoclonal antibody is selected from the group consisting of murine and humanized monoclonal antibodies.

11. The monoclonal antibody according to claim 10 that, when used with an immobilized CD3 monoclonal antibody in a T-cell co-stimulation stimulation assay, costimulates the proliferation of T-cells equivalent to or better than interleukin 2.

12. The monoclonal antibody according to claim 11 that in solution causes less than 10% lysis of Fas-expressing cells.

13. The monoclonal antibody according to claim 12 that when crosslinked by immobilization causes less than 30% lysis of Fas-expressing cells.

14. The monoclonal antibody according to claim 12 that at about a 10 µg/ml concentration inhibits greater than 90% of Fas ligand-mediated lysis of Fas-expressing cells.

15. A monoclonal antibody selected from the group consisting of the monoclonal antibody M38 produced by the hybridoma ATCC HB 11465, and monoclonal antibodies having all of the biological characteristics of M38.

16. An IgG1 monoclonal antibody the at specifically binds to the extracellular domain of human Fas antigen and is able to block greater than 90% of Fas-ligand-mediated lysis of cells expressing Fas antigen.

17. The monoclonal antibody according to claim 16, wherein said monoclonal antibody is able to block greater than 90% of anti-Fas monoclonal antibody CH-11-mediated lysis of cells expressing Fas antigen.

18. An antigen-binding fragment of the monoclonal antibody according to claim 1.

19. A humanized monoclonal antibody comprising the antigen binding site of the monoclonal antibody according to claim 1, and the constant region of a human monoclonal antibody of the IgG4 subclass.

20. A monoclonal antibody (mAb) selected from the group consisting of M3, produced by hybridoma ATCC HB 11726, M38, produced by hybridoma ATCC HB 11465 antigen-binding fragments of M3, antigen-binding fragments of M38, humanized mAbs derived from M3, and humanized mAbs derived from M38.

21. The mAb according to claim 20, wherein said mAb is selected from the group consisting of M38, produced by hybridoma ATCC HB 11465, antigen-binding fragments of M38, and humanized mAbs derived from M38.

22. A composition comprising the mAb according to claim 20, a physiologically acceptable diluent or carrier.

23. The mAb according to claim 3 that at about a 10:1 molar ratio inhibits anti-Fas CH-11 mAb-mediated lysis of cells by greater than 50%, and that at a 10 µg/ml concentration inhibits greater than 90% of Fas ligand-mediated lysis of Fas-expressing cells.

24. A hybridoma cell line selected from the group consisting of the hybridoma cell line deposited as ATCC HB 11465 and the hybridoma cell line deposited as ATCC HB 11726.

25. A mAb selected from the group consisting of the mAb M3 produced by the hybridoma ATCC HB 11726, and mAbs having all of the biological characteristics of M3.

* * * * *